United States Patent
Liotta et al.

[11] Patent Number: 5,942,407
[45] Date of Patent: Aug. 24, 1999

[54] LIGHT-EMITTING IMMUNOASSAY

[75] Inventors: Lance A. Liotta, Potomac; Bryan C. Christiansen, Gaithersburg; Alan R. Day, North Potomac, all of Md.; Tabitha Harlacher, Herndon; Katherine Paweletz, Alexandria, both of Va.

[73] Assignee: Immunomatrix, Inc., Washington, D.C.

[21] Appl. No.: 08/882,594

[22] Filed: Jun. 25, 1997

Related U.S. Application Data

[60] Provisional application No. 60/020,387, Jun. 25, 1996.

[51] Int. Cl.⁶ ............................. C12Q 1/28; C12Q 1/00; G01N 33/53
[52] U.S. Cl. ..................... 435/28; 435/7.1; 435/4; 435/8; 422/55; 422/50; 422/68.1; 422/52; 422/82.05
[58] Field of Search ................... 435/28, 7.1, 4, 435/8; 422/55, 50, 68.1, 52, 82.05

[56] References Cited

U.S. PATENT DOCUMENTS

| | | | |
|---|---|---|---|
| 4,391,904 | 7/1983 | Litman et al. | 435/28 |
| 4,446,232 | 5/1984 | Liotta | 435/28 |
| 4,587,099 | 5/1986 | Rothe et al. | 435/28 |
| 4,594,224 | 6/1986 | Okaniwa et al. | 435/28 |
| 4,604,364 | 8/1986 | Kosak | 435/28 |
| 4,623,461 | 11/1986 | Hossom et al. | 435/28 |
| 4,631,174 | 12/1986 | Kondo | 435/28 |
| 4,654,310 | 3/1987 | Ly | 435/28 |
| 4,673,657 | 6/1987 | Christian | 435/28 |
| 4,678,757 | 7/1987 | Rapkin et al. | 435/28 |
| 4,710,458 | 12/1987 | Maines | 435/28 |
| 4,761,381 | 8/1988 | Blatt et al. | 435/28 |
| 4,764,462 | 8/1988 | Bredehorst et al. | 435/28 |
| 4,770,853 | 9/1988 | Bernstein | 435/28 |
| 4,788,140 | 11/1988 | Findlay et al. | 435/28 |

(List continued on next page.)

FOREIGN PATENT DOCUMENTS

| | | |
|---|---|---|
| 37 22 873 | 4/1989 | Germany . |
| WO9609927 | 4/1996 | WIPO . |

OTHER PUBLICATIONS

*Methods in Enzymology*, Vo. 133, 1986, "Enhanced Chemiluminescent Reactions Catalyzed by Horseradish Peroxidase", Thorpe et al.

*Methods in Enzymology*, vol. 133, 196, "Photographic Detection of Chemiluminescent and Bioluminescent Reactions", Kricka et al.

(List continued on next page.)

*Primary Examiner*—Louise N. Leary
*Attorney, Agent, or Firm*—Fay, Sharpe, Beall, Fagan, Minnich & McKee

[57] ABSTRACT

A light generating dry disposable device for determining the presence of analytes in a test sample is disclosed. The device comprises a first zone containing conjugated ligand which is capable of reacting with analytes in the test sample. The ligand is conjugated with a photoprotein or related enzyme. The device further comprises a second trapping zone comprising immobilized analyte. The device also includes a third zone containing a reporter system that activates light generation by the conjugate. The conjugates are maintained in the first zone such that they are removable from the first zone when reacted with the soluble analytes from the test sample passing through the first zone, but not removed from the second trapping zone in the absence of such analytes. The third zone contains material capable of reacting with the photoprotein- or enzyme-linked ligand to produce a light-emitting reaction which indicates the presence of the analyte being tested. The present invention provides dry flow through zones. The trapping zone is juxtaposed with the light activation zone such that only formed analyte conjugate complexes enter the light activation zone. Also disclosed is the use of a luminometer for measuring the amount of light generated from the assay device upon detection of analyte. Other provisions are disclosed for recording and quantifying the amount of analyte, such as for example, photographic film.

30 Claims, 14 Drawing Sheets

U.S. PATENT DOCUMENTS

| | | | |
|---|---|---|---|
| 4,803,154 | 2/1989 | Uo et al. | 435/28 |
| 4,818,677 | 4/1989 | Hay-Kaufman et al. | 435/28 |
| 4,820,489 | 4/1989 | Rothe et al. | 435/28 |
| 4,837,145 | 6/1989 | Liotta | 435/28 |
| 4,863,689 | 9/1989 | Leong et al. | 435/28 |
| 4,935,339 | 6/1990 | Zahradnik | 435/28 |
| 4,956,275 | 9/1990 | Zuk et al. | 435/28 |
| 4,978,502 | 12/1990 | Dole et al. | 435/28 |
| 5,023,181 | 6/1991 | Inouye | 435/28 |
| 5,035,866 | 7/1991 | Wannlund | 435/28 |
| 5,093,240 | 3/1992 | Inouye et al. | 435/28 |
| 5,139,937 | 8/1992 | Inouye et al. | 435/28 |
| 5,200,334 | 4/1993 | Dunn et al. | 435/28 |
| 5,486,455 | 1/1996 | Stults | 435/28 |
| 5,683,888 | 11/1997 | Campbell | 435/29 |

OTHER PUBLICATIONS

*Analytical Biochemistry 194,* 185–191 (1991), "A Solid–Phase Assay for β–1, 4–Galactosyltransferase Activity in Human Serum Using Recombinant Aequorin", Zatta et al.

*Proc. Natl. Acad. Sci. USA,* vol. 83, pp. 8107–8111, Nov. 1986 Biochemistry, "Site–specific mutagenesis of the calcium–binding photoprotein aequorin", Tsuji et al.

*Proc. Natl. Acad. Sci. USA,* vol. 86, pp. 80–84, Jan. 1989 Biochemistry, "Bioluminescence of the $Ca^{2+}$–binding photoprotein aequorin after cysteine modification", Kurose et al.

*Biochemical and Biophysical Research Communications,* vol. 174, No. 3, 1991, Feb. 14, 1991, pp. 1331–1336, "Bioluminescent Immunoassay Using a Monomeric Fab'–Photoprotein Aequorin Conjugate", Erikaku et al.

*Journal of Bioluminescence and Chemiluminescence,* vol. 4, pp. 512–522 (1989), "The Use of a CCD Imaging Luminometer in the Quantitation of Luminogenic Immunoassays", Leaback et al.

*Proc. Natl. Acad. Sci. USA,* vol. 75, No. 6, pp. 2611–2615, Jun. 1978 Biochemistry, "Perosidized coelenterazine, the active group in the photoprotein aequorin", Shimomura et al.

*Biochemistry 1984,* 23, 4383–4390, "Electron Paramagnetic Resonance of Spin–Labeled Aequorin", Kemple et al.

*Nature,* vol. 338, Apr. 13, 1989, "Chemiluminescence lights up".

*Proc. Natl. Acad. Sci. USA,* vol. 87, pp. 2047–2051, Mar. 1990 Biochemistry, "Expression and secretion of aequorin as a chimeric antibody by means of a mammalian expression vector" Casadei et al.

*Biochemistry 1992,* vol. 31, pp. 1433–1442, "Use of Recombinant Biotinylated Aequorin in Microtiter and Membrane–Based Assays: Purification of Recombinant Apoaequorin from *Escherichia coli*" Stults et al.

Fagan et al; Federation of European Biochemical Societies, vol. 333 No. 3, pp. 301–305, 1993.

Moisescu et al; Biochimica et Biophysica Acta, vol. 396, (1975), pp. 133–140.

RADIAL FLOW INTEGRAL CCD FORMAT

BUBBLE FORMAT

DIGOXIN ASSAY: DOSE DEPENDENT TIME COURSE
OF LIGHT GENERATION
AEQUORIN CONJUGATE DRY CALCIUM ACTIVATION ZONE

DOSE DEPENDENT FILM RECORDING
OF DIGOXIN ASSAY

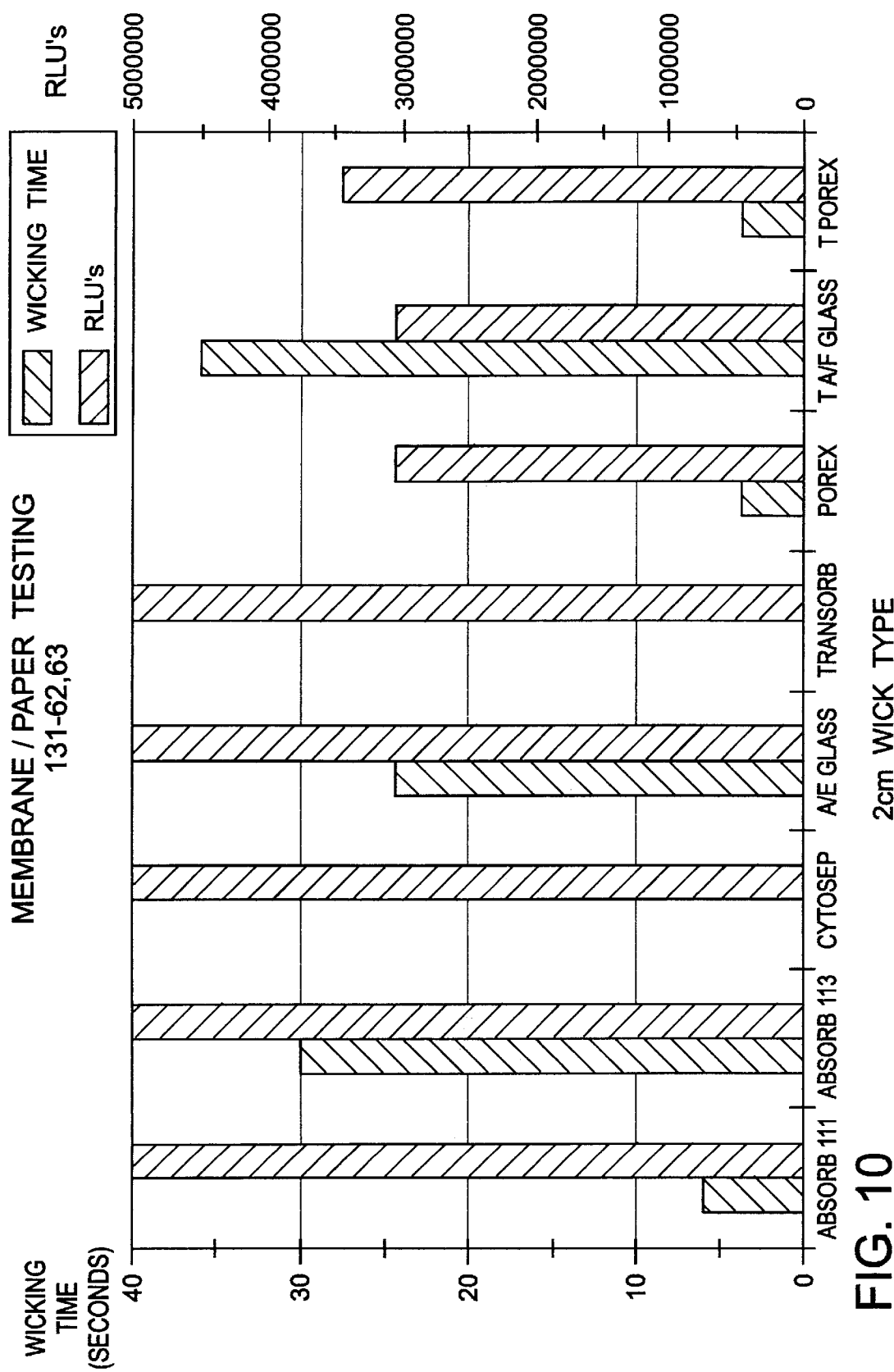

LIGHT-EMITTING IMMUNOASSAY

CROSS REFERENCES TO RELATED APPLICATIONS

The present application claims priority from U.S. Provisional application No. 60/020,387 filed Jun. 25, 1996.

BACKGROUND OF THE INVENTION

1. Field of the Invention

The present invention relates to test devices that utilize a biochemical interaction between antigens and antibodies or fragments thereof to determine the presence of a target analyte. The invention also relates to methods for determining the presence of a target analyte in a biological fluid. More particularly, the invention relates to the use and activation of photoproteins to emit light in a localized region of a diagnostic assay device.

2. Description of the Related Art

Rapid and accurate determination of the presence or concentration of target analytes in biological fluids has drawn increasing attention in recent years. Enzyme Linked Immunosorbent Assay (ELISA) techniques employ an enzyme label which is used as a detection marker. Differing ELISA formats have been developed, but all employ an enzyme label, a detection means for determining the presence of the label, and a specific immunological binding reaction of an antigen-antibody pair. Although these assays can be somewhat simpler for laboratory technicians relative to other techniques for detecting the presence of an analyte species, these assays can be lengthy and can involve several steps and reagents. Accordingly, single step assays are desirable.

The traditional wet chemical method for detection of biological substances such as hormones, metabolites, ethical drugs, drugs of abuse, antibodies, and antigens, have, in some instances, been replaced by dry test strips which are conformed to generate a signal upon application of a test fluid containing target analyte. As will be appreciated, dry test strips are simple and convenient. However, the usual readout from such strips is a line or spots of color and not a light reaction. This is because previous assay devices have not provided a separate dry phase zone which can activate light generation by conjugated ligand that has reacted with analyte.

One recently developed dry strip method, disclosed in U.S. Pat. No. 4,446,232 to Liotta, hereby incorporated by reference, provides a technique for obtaining a rapid and reliable indication of analyte presence. Although satisfactory, there is still a need for an improved technique, particularly one which provides superior sensitivity of detecting the presence or concentration of analyte. Moreover, there is a need for an improved technique for signaling or indicating the presence or concentration of analyte.

The binding of ligand pairs, such as an analyte in a test sample and antibodies in a diagnostic assay, can be measured by labeling one member of the ligand pair with a photoprotein which produces light as a signal for detection. A bioluminescent protein particularly useful in labeling reagents for diagnostic assays is aequorin, as described in U.S. Pat. No. 5,486,455 to Stultz, hereby incorporated by reference. In the past, aequorin has been used to label antibodies and was found useful in standard format immunoassays in which aequorin labeled molecules were detected in solution by a luminometer. Photoproteins must be activated to emit light. Aequorin is activated by calcium ions, typically in the form of a solution of calcium acetate. For conventional tube luminometer measurements, the calcium acetate solution is squirted into a liquid solution containing an aequorin conjugated reagent. The addition of calcium acetate must take place in the dark so that ambient light does not reach the photomultiplier tube. Upon addition of calcium, the photoprotein flashes and the light is recorded by the luminometer.

The application of aequorin photoproteins in the prior art for diagnostic assays has been in the form of a kit utilizing several liquid reagents. The prior assay kits require multiple incubation and washing steps, introduction of liquid calcium solution in the dark, and quantitation of the signal by a tube luminometer. In this prior form, a light emitting analyte detection system could not be applied to rapid disposable diagnostic devices. Diagnostic assays in the prior art employing the activation of photoproteins require complicated multi-reagent kits, time consuming multiple steps, and quantitation by high cost luminometers. Accordingly, there is a need for an easy to use, one step, economical dry and disposable diagnostic assay that emits light to indicate the presence of an analyte.

SUMMARY OF THE INVENTION

A general objective of the present invention is to provide a dry disposable one step diagnostic device employing light emission to indicate the presence of one or more target analytes. Another general objective is to provide a one step diagnostic assay device that does not require washing steps or the need to introduce a photoprotein activation solution into the device. A further objective is to provide a one step diagnostic assay device that produces a visual indication of analyte concentration, and which, is readily recordable such as with photographic film. A further objective is to provide a dry disposable diagnostic device utilizing photoprotein activation which can be quantitated by a luminometer that measures light emitted from a surface of the device.

Specifically, the present invention provides, in a first aspect, a method for activating light emission by a photoprotein used in a diagnostic assay. The method involves providing a substrate with a dried salt of a metal cation or a caged metal cation. The substrate is then hydrated with a liquid comprising a photoprotein labeled reagent, thereby releasing metal cation and allowing reaction with the photoprotein labeled reagent to generate light. The substrate is preferably juxtaposed with a trapping zone such that only formed analyte-photoprotein conjugate complexes will enter the substrate light activation zone.

In another aspect, the present invention provides a process for triggering light emission from a signal generating label utilized in a diagnostic device. The process involves providing a first substrate containing a dried signal generating labeled reagent, the signal generating label being peroxidase for example. A second substrate containing a light emitting substance such as luminol is provided and disposed proximate to the first substrate. The first substrate is hydrated thereby releasing the signal generating labeled reagent from the first substrate into the second substrate. The signal generating labeled reagent reacts with the light emitting substance in the second substrate to emit light.

In yet another aspect, the present invention provides a diagnostic device adapted for producing a visual indication of analyte concentration in a liquid test sample. The device comprises a first substrate or region thereof comprising signal generating labeled ligands or antibodies. The device further comprises a second substrate or region proximate to the first substrate, comprising immobilized analyte or antigens adapted for binding the signal generating labeled ligands or antibodies. The device further comprises a third substrate or region proximate to the second substrate, comprising an activating agent capable of reacting with the signal generating labeled ligands or antibodies. Upon such reaction, light is emitted from the diagnostic device.

In yet an additional aspect, the present invention provides an apparatus for quantifying analyte concentration in a liquid test sample. The apparatus comprises a diagnostic device, such as the previously described device, and a luminometer in sufficiently close proximity to the diagnostic device, and particularly, a surface of the device from which light is emitted, to detect light emitted from the device. In addition, or instead of the luminometer, image recording provisions such as a CCD camera and photographic film are also provided to use in combination with the light emitting diagnostic devices of the present invention.

Still other advantages and benefits of the invention will become apparent to those skilled in the art upon a reading and understanding of the following detailed description.

BRIEF DESCRIPTION OF THE DRAWINGS

FIG. 10 illustrates results of testing of several commercially available substrate materials.

DETAILED DESCRIPTION OF THE PREFERRED EMBODIMENTS

In one aspect, the present invention provides an immunoassay device and a luminometer for measuring light emitted from a surface of the immunoassay device.

Immunoassay Device

In a preferred embodiment, the reagents of the assay are impregnated into a multi-zoned test strip. A first zone, referred to herein as a "signal generating zone," comprises soluble ligand conjugated with a signal generating label, which is typically a photoprotein or an enzyme thereof. A second zone, referred to herein as a "trapping zone," comprises immobilized analyte. A third zone, referred to herein as a "reporter system zone," is utilized to indicate the presence of labeled ligand complexed with analyte from a sample undergoing testing. The reporter system preferably utilizes a light-emitting reaction to indicate the presence of analyte.

The liquid sample to be tested and so potentially containing analytes, is placed in contact with the signal generating zone and allowed to passively flow into the test strip. Soluble photoprotein- or enzyme-linked ligands, such as antibodies, which have recognition sites, are allowed to mix with the test sample and flow from the signal generating zone into the trapping zone. Conjugated ligand with free binding sites is trapped in the trapping layer by bonding to the immobilized analyte. In contrast, only complexes formed between the conjugate and analyte in the test sample are not trapped. Therefore, the amount of photoprotein- or enzyme-linked ligands, e.g. antibodies, that ultimately reach the third zone containing the reporter system or a component thereof, depends on the concentration of the analyte in the test sample. An activating agent in the dry zone reporter system reacts with the photoprotein or enzyme from the photoprotein- or enzyme-linked ligands having reached the third zone, thereby emitting light.

The photoprotein- or enzyme-linked antibodies are maintained in the first zone in such a manner that they are capable of being removed from the first zone. When reacted with analyte, such as from a sample being tested, the conjugated photoprotein, or enzyme-linked antibody enters and passes through the second zone and into the third zone. Without analyte, the photoprotein- or enzyme-linked antibodies are complexed with bound antigens in the second zone and so, cannot reach the third zone.

Figure 1A:
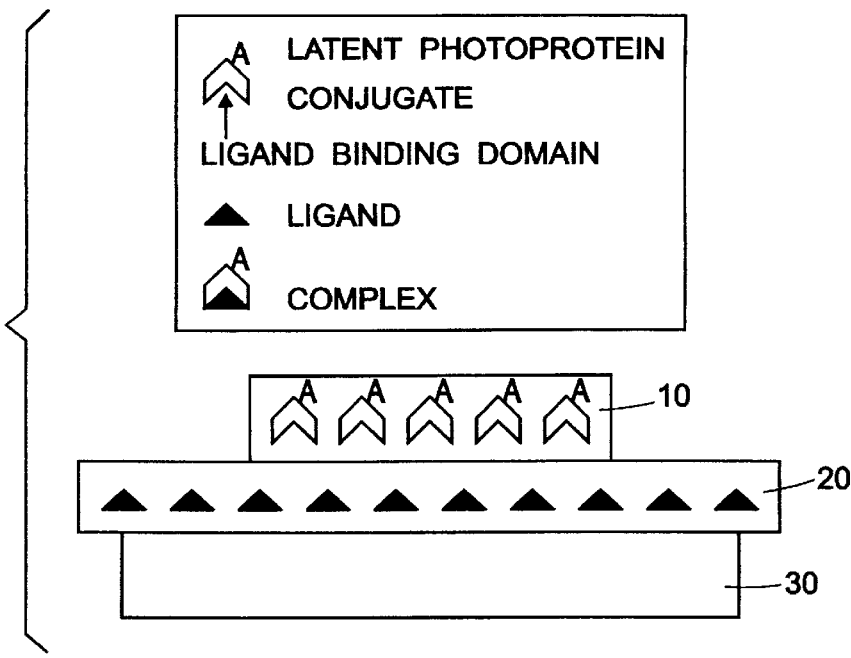
FIG. 1A is a schematic representation of a preferred immunoassay device in accordance with the present invention.

In a preferred embodiment of the present invention, the immunoassay device comprises a sandwich arrangement of three, porous matrix layers as illustrated in FIG. 1A. A first porous layer 10 corresponding to the signal generating zone, is impregnated with a specific antibody linked with a photoprotein or a suitable enzyme. A second porous layer 20 serving as the trapping zone, contains immobilized (bound) reference antigen. The antigen is of the type specifically recognized by the antibody in the first porous layer. A third layer 30 corresponding to the reporter system zone, contains a light emitting substance or activating agent that reacts with the photoprotein or enzyme linked to the antibody.

Figure 1B:
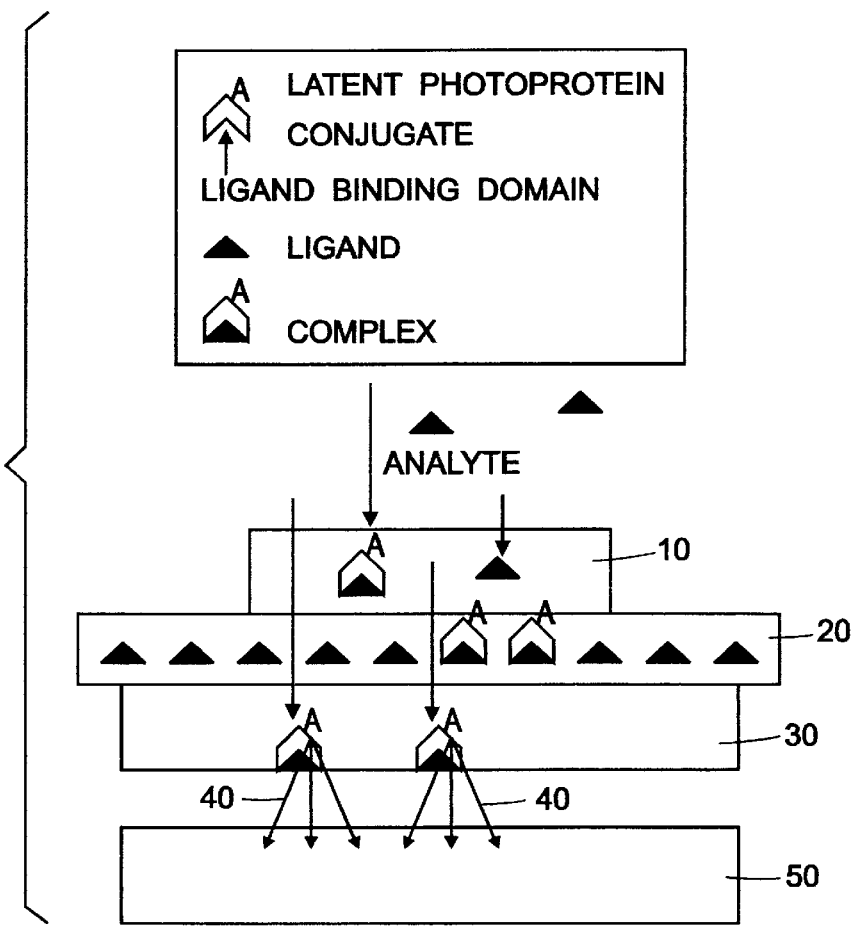
FIG. 1B is a schematic representation of the immunoassay device depicted in FIG. 1A utilized in conjunction with a luminometer for detecting light emitted from the device.
Figure 1C:
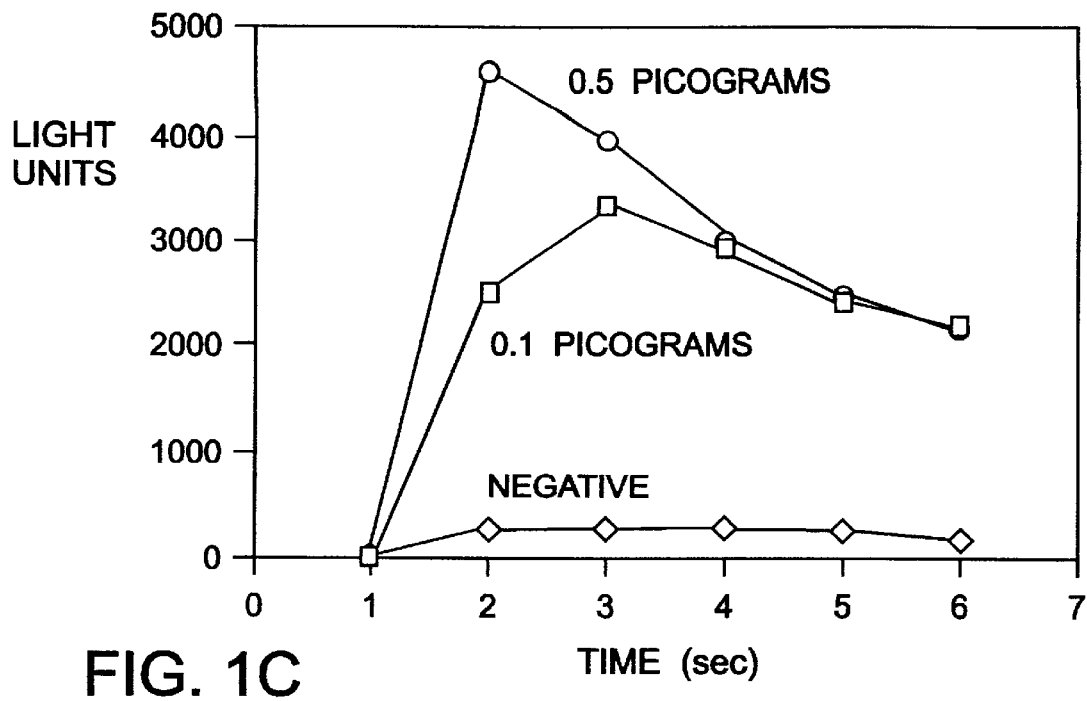
FIG. 1C illustrates light emission from the device of FIG. 1A.
Figure 1D:
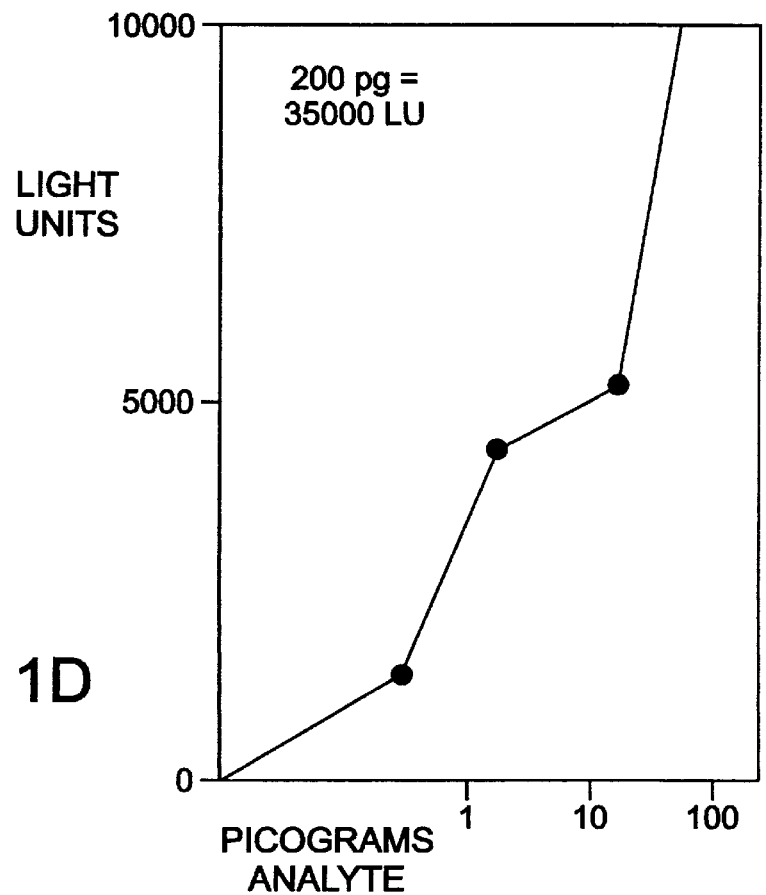
FIG. 1D illustrates the sensitivity of the device of FIG. 1A.

The process by which the preferred embodiment immunoassay device operates is as follows. Referring to FIG. 1B, a fluid sample, containing the analyte to be tested, is placed in contact with the first layer 10. Free analyte in the test sample flows into the second layer 20. Hydration by the fluid test sample induces or promotes photoprotein- or enzyme-linked antibodies in the first layer 10 to move into the second layer 20. The unoccupied conjugate binds to the reference antigen (analyte) in the second layer 20. If the photoprotein- or enzyme-linked antibodies have combined with free analyte, the conjugated product will freely travel into the third layer 30 and produce a light emitting reaction. The duration of peak light emission is typically at least about 1 second and as long as 5 to 10 seconds. The length of time of light generation is about 1 second to about 90 seconds for aequorin based conjugates. The intensity of light produced is proportional to the amount of analyte in the test sample. This is illustrated in FIGS. 1C and 1D. If the fluid sample does not contain analyte, all the photoprotein- or enzyme-linked antibodies having traveled from the first layer 10, will combine with the immobilized analyte in the second layer 20. Photoprotein- or enzyme-linked antibodies which combine with the immobilized antigen in the second layer 20 will not flow into the third layer 30, and the light emitting reaction will not be produced. As explained in greater detail below, a photomultiplier, luminometer, or light detector 50 is preferably utilized to detect, measure, and/or quantify photons 40 emitted from the third layer 30.

Analyte-Antigen

A typical analyte or antigen detected by the preferred embodiment immunoassay device of the present invention is characterized by being monoepitopic or polyepitopic. Polyepitopic analytes are typically large molecule polypeptides, polysaccharides, polynucleic acids, or combinations thereof. Other analytes can be somatic cells, germ cells, bacteria, viruses, and other cellular units. Sub-cellular units which can be analytes include viral coat protein, cell wall polysaccharide, DNA, DNA segments, transfer RNA, messenger RNA, mitochondrial DNA, mitochondria, cell nuclei, cell membrane, ribosome, and other varied cell organelles, sub-units and constituent parts. Such polyepitopic analytes detected by the invention typically can have molecular weights in excess of about 50,000. Many such analytes can have a molecular weight ranging from 50,000 to 5,000,000 and more.

The preferred embodiment immunoassay device can also be used to detect and quantitate the presence of smaller molecular analyte, such as molecules with a molecular weight less than about 50,000, and typically between 5,000 and 50,000. The device can be used to analyze for the presence of virtually any analyte that can elicit an antibody response. The analyte can be either the antigen or an epitope-containing fragment thereof.

A wide variety of natural proteins and protein sub-units can be detected using the preferred embodiment device. Such proteins include histones, globulins, nucleoproteins, lipoproteins, glycoproteins, somatotropin, prolactin, insulin, pepsin, human plasma protein constituents including human albumen, thyroxin binding globulin, haptoglobin, ceruloplasmin, cholinesterase, myoglobin, fibrinogen, plasminogen, poly- and monoclonal immunoglobulins of the A, D, E, G or M classes, free light or heavy chains of the immunoglobulins, an Fab fragment or an F(ab')$_2$ fragment, variable regions, hyper variable regions, or constant regions of the immunoglobulin; complement factors, blood clotting factors such as thromboplastin (factor III), Christmas factor (factor IX), and others; peptide and protein hormones including glucagon, erythropoietin, FSH, LH, kinetotropins including HCG, oxytocin, and vasopressin. Clearly, any protein or protein sub-unit that can generate an antibody in poly- or monoclonal antibody techniques can be used in the present invention.

Antigenic polysaccharides derived typically from cell walls of pathogens (such as virus, bacteria, yeasts, fungi) can act as antigens. Such cell-wall antigens can be detected in strains of microorganisms such as Strepylococcus, Corynebacterium, Haemophilus, Klebsiella, Salmonella, Candida yeasts, Actinomycetes fungi, pneumococcus, Streptococcus, Staphylococcus, Anthrobacteria, and others.

Small molecules of natural and synthetic origin, typically monoepitopic analytes having a molecular weight of about 100 to 5,000, and typically, 100 to 2,000, can also act as an analyte. Such analytes include small molecule natural biochemicals; ethical, over the counter drugs, the illicit drugs, hormones, peptides, mono- and disaccharides, metabolites, pesticides, pollutants, and other organic synthetic chemicals, etc. Drugs of interest include alkaloids such as morphine, codeine, heroin, dextromethorphan, derivatives and metabolites. Also included are ergot alkaloids such as LSD, steroid alkaloids, quinoline alkaloids and others. Ethical drugs of interest include steroids, bile acids, digoxin, diethylstilbestrol, ethynylestradiol, and others. Other drugs include barbiturates such as phenolbarbitol, secobarbital, and others. Additionally, drugs such as amphetamines, catechol amines, L-dopa, epinephrin, chlorpromazine, benzodiazipines, phenolthiazines, theophylline, caffeine, cannabis drugs such as cannabinol, tetrahydrocannabinol, vitamins, prostaglandins, antibiotics, such as penicillin, and the penicillin variants, cephalosporin and the cephalosporin variants, chloromycetin, actinomycetin, tetracycline, nucleosides and nucleotides, fragments and derivatives thereof including ATP, AND, FMN, AZTP, and others. Additionally, drugs including methadone, meprobamate, serotonin, lidocaine, propranolol, antihistamines, antichlorinergic drugs, and others can be detected.

Antibody

Antibodies for use in the preferred embodiment immunoassay devices of the present invention can be prepared by well-known polyclonal and monoclonal antibody techniques. Polyclonal antibodies can be raised in a variety of test animals including mice, rats, rabbits, horses and others. Monoclonal antibodies can be prepared using well-known techniques such as those disclosed by Kohler and Milstein, "Continuous Cultures of Fused Cells Secreting Antibody of Predetermined Specificity," *Nature,* Vol 256, pp. 495–497, Aug. 7, 1975, hereby incorporated by reference.

In accordance with the present invention, it is preferred to utilize a modified antibody. Such modified antibodies exhibit increased affinity for conjugation such as with a signal generating ligand such as a photoprotein. A preferred technique for antibody modification is as follows. The antibody is modified by sulphosuccinimidyl 4-(N- maleimidomethyl) cyclohexane-1-carboxylate (SSMCC) to produce a maleimide-enzyme conjugate. Next, PDP-Hydrazide (3[2-Pyridyldithio] propionyl hydrazide) is utilized to add a sulfhydryl group to a carbohydrate moiety of the antibody. Next, the sulfhydryl group is reduced, such as by reaction with 2-MEA. The modified antibodies can then be conjugated with a signal generating label such as a peroxidase agent.

It has been discovered that this modification technique produces an antibody conjugate having significantly improved binding ability. When the previously described modified and conjugated antibodies are passed through a column to remove free peroxidase, such as in the form of horseradish peroxidase (HRP), the resulting collected modified conjugated antibodies incorporated into the present invention immunoassay device, produce light signals or images with enhanced signal to background ratios. An exemplary technique for modifying an antibody in accordance with this technique is set forth in the examples herein.

The present invention provides another technique for modifying an antibody. This technique is directed to modifying the antibody at a site distal to the binding component. Specifically, the technique relies upon oxidation of the carbohydrate entity in the vicinity of the F region. Sodium periodate is utilized to introduce aldehyde groups into the carbohydrate which can then react with hydrazine (or amine) entities in the modified aequorin. A significant advantage in using hydrazine or amine is their low $pK_a$ (about 3 to 4), i.e., hydrazides react preferentially with aldehydes at acidic pH (the $PK_a$ of amine is about 9.0).

Specifically:

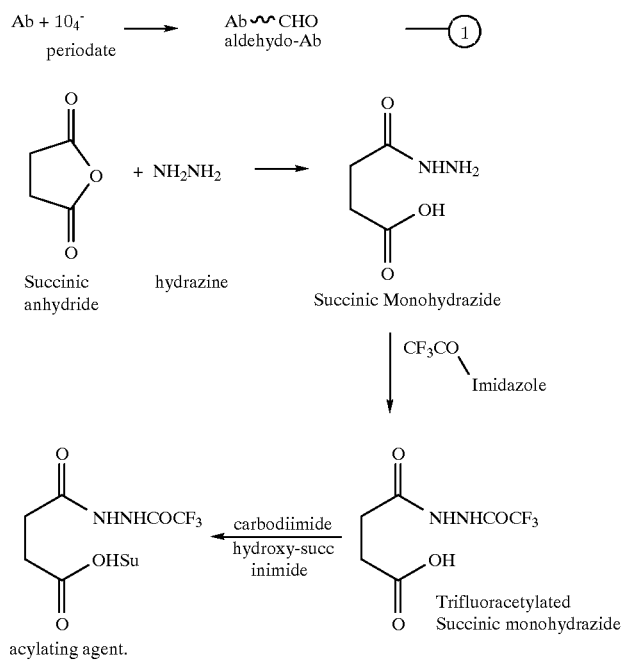

It is contemplated that other bifunctional reagents of formula (I) set forth below could be used for antibody modification besides SSMCC.

$$H_2NHNC(a) \ (CH_2)_xC(b) \ S\text{—}S\text{—}R' \quad (I)$$

Where a=$H_2$;HR;O
b=$H_2$
x=an integer equal to or greater than 1
R'=a stable leaving group Additional aspects of the antibody modification techniques of the invention include the following. The initially formed hydrazone is reduced with cyanoborohydride in situ. This is referred to as reduction alkylation. Other suitable reagents are the diboranes such as for instance, pyridine diborane. This will enhance the stability of the initial Schiff's base, particularly at acidic pH. Any unreacted aldehyde groups can be quenched, following reaction of the antibody aldehydes with PDPH, by treatment with ethanolamine, to prevent aggregation of conjugate.

Reporter System

The reporter system preferably comprises one or more photoproteins or related enzymes and one or more activating agents. The photoproteins or related enzymes are initially maintained in the signal generating zone. As previously noted, the photoproteins or enzymes are conjugated to soluble antibodies initially maintained in the signal generating zone. Upon reaction with a suitable analyte, such as from a sample being tested, the conjugated analyte—(photoprotein or enzyme)—antibody travels through the trapping zone, and reaches the reporter system zone. Maintained in the reporter system zone is one or more activating agents, i.e. a substance or agent that induces or undergoes a light-emitting reaction with the photoprotein or related enzyme.

A preferred photoprotein for use in the preferred embodiment immunoassay device is aequorin. This photoprotein originates from jellyfish. Aequorin is documented in the literature. Kemple, et al., "Electron Paramagnetic Resonance of Spin-Labeled Aequorin," *Biochemistry*, 23, p. 4383–4390, 1984; Shimomura, et al., "Peroxidized Coelenterazine, the Active Group in the Photo protein Aequorin," *Proc. Natl. Acad. Sci. USA*, vol. 75, No. 6, p.

2611–2615, June 1978; Tsuji, et al., "Site-Specific Mutagenesis of the Calcium-Binding Photo protein Aequorin," *Proc. Natl. Acad. Sci. USA,* vol. 83, p. 8107–8111, November 1986; and Kurose, et al., "Bioluminescence of the $Ca^{2+}$—Binding Photo protein Aequorin After Cystene Modification," *Proc. Natl. Acad. Sci. USA,* vol. 86, p. 80–84, January 1989; all of which are hereby incorporated by reference.

Other photoproteins are suitable for use in the reporter system besides aequorin. Examples include, but are not limited to, obelin, mitrocomin, and clytin. These photoproteins apparently also originate from jellyfish. Obelin is documented in the literature, *Arch. Biochem. Biophys.,* 316 (1), p. 92–99, 1995, hereby incorporated by reference. Mitrocomin is documented such as for instance, *FEBS Letters,* 333(3), p. 301–305, 1993, hereby incorporated by reference. Clytin is also documented, *FEBS Letters,* 315(3), p. 343–346, 1993, hereby incorporated by reference.

In an alternative embodiment, the soluble antibody initially maintained in the signal generating zone can be conjugated or labeled with peroxidase or other suitable agent as a signal generating label. A preferred peroxidase is horseradish peroxidase (HRP). An effective amount of luminol (5-amino-2,3-dihydro-1, 4-phthalazinedione) can be incorporated in the reporter system zone, and serve as a light emitting substance. In the event of the peroxidase conjugate reaching the reporter system zone, the luminol reacts with the peroxidase to generate light. It is also contemplated that one or more other unstable oxygen species may be utilized in addition to, or instead of, a peroxidase agent. Examples of such species include $O_2^-$, $H_2O$, and $OH^-$.

In another alternate embodiment, a system comprising urea hydrogen peroxide, enhanced luminol, and an antibody coupled to HRP is utilized. Urea hydrogen peroxide is preferred since it is stable when applied in a solution of methanol or acetone and deposited on a paper substrate, and preferably incorporated within the signal generating zone. The urea hydrogen peroxide remains active or stable when dried down onto the paper substrate. Upon hydration of the immunoassay device, i.e., application of an aqueous test sample, urea hydrogen peroxide releases hydrogen peroxide upon contact with water. Hydrogen peroxide activates HRP, which as described above, is coupled to soluble antibody initially maintained in the signal generating zone. An effective amount of enhanced luminol is incorporated in the reporter system zone. In the event of the HRP-antibody conjugate reaching the reporter system zone, the luminol reacts with the peroxidase to generate light.

Aequorin is the preferred photoprotein. Recombinant aequorin is available commercially from Sealite Sciences, Inc. of Bogart, Ga. and RBI. Upon activation, such as by divalent calcium $Ca^{+2}$, aequorin emits light as a result of an intramolecular reaction in which coelenterazine, an imidazopyrazine compound bound noncovalently to the protein, is oxidized to coelenteramide, thereby yielding light having a maximum wavelength of about 470 nm, $CO_2$, and a blue fluorescent protein. The wavelength of light emitted by aequorin is generally in the range of from about 440 to about 475 nm. The excited state of coelenteramide bound to the protein is the emitter in the reaction. The amount of light generated is proportional to the amount of photoprotein activated. For aequorin, the amount of light generated upon activation, in relative light units (RLU), is about 200 RLU per atom mole.

The rate or response of light emission, and the wavelength of light emitted from the reaction can be modified by replacing coelenteramide with coelenteramide analogues. These techniques are described in the literature, *Biochem J.,* 306, pt. 2, p. 537–543, 1995; *Cell Calcium,* 14(5), p. 373–378, 1993; and *Cell Biology,* 121(1), p. 83–90, 1993; all of which are hereby incorporated by reference. Coelenteramide analogues are commercially available, such as for instance, from Molecular Bioscience. These analogs are generally designated as h and e type aequorins. These analogs exhibit different sensitivities to $Ca^{+2}$ and also demonstrate bi-modal luminescence with peaks at 400–405 nm and 440–475 nm. h-Coelenterazine aequorin is more sensitive to $Ca^{+2}$ as compared to e type.

Figure 2:
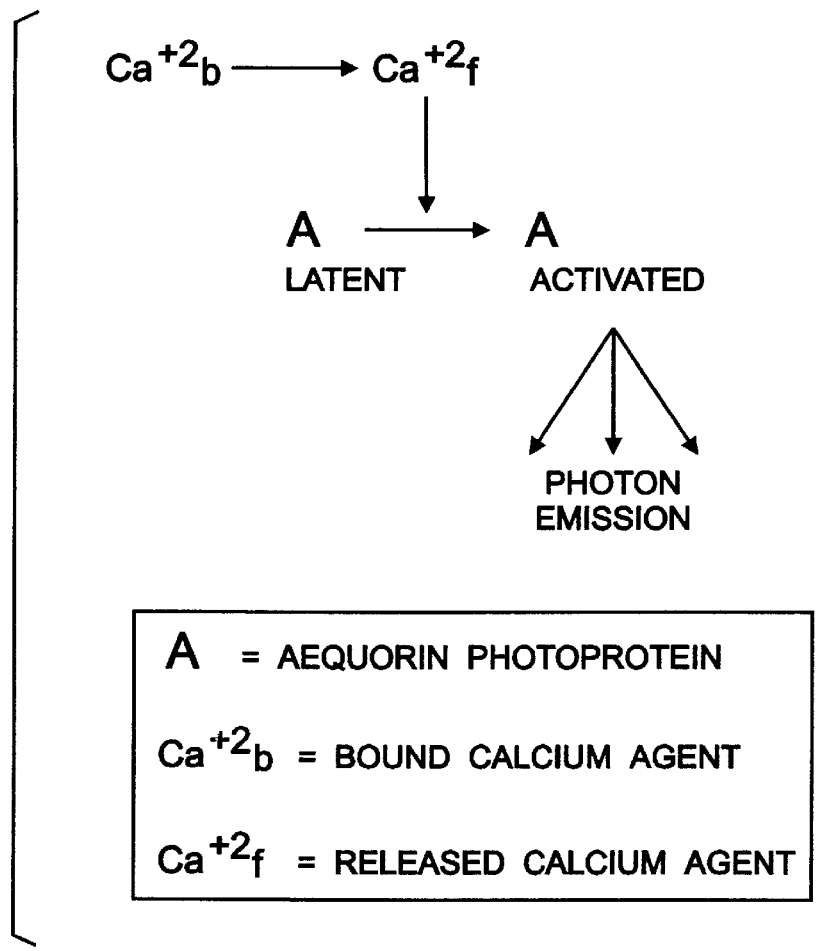
FIG. 2 illustrates a reaction between a photoprotein and an activating agent.

FIG. 2 illustrates reaction between a photoprotein and an activating agent such as calcium. The photoprotein enzyme substrate complex is maintained in a latent state by the absence of calcium ions and preferably in the presence of calcium chelating compounds such as EDTA in the signal generating zone. When the soluble photoprotein encounters the reporter system zone, calcium ions are locally released from an immobilized state. The released calcium activates the photoprotein resulting in local light emission. As explained in greater detail below, a light detection means is preferably provided which is in close proximity with the reporter system zone.

In order to utilize aequorin in the reporter system of the preferred embodiment immunoassay device, it is preferred to chemically modify aequorin. One such technique for modifying aequorin is described in U.S. Pat. No. 5,486,455 to Stults, previously hereby incorporated by reference. The modification is performed to promote conjugation between a modified antibody and aequorin. According to that patent, aequorin is modified by first reacting with iminothiolane (Traut's reagent) which introduces —SH groups into the molecule. The modified antibody such as SSMCC—Ab, is then reacted with the modified aequorin (the maleimide function reacts with the sulphydryl group) to form the desired conjugate. A significant aspect of the selection of iminothiolane for modifying aequorin is that iminothiolane does not interfere with the photolytic activity of aequorin.

The present invention provides an alternative modification technique whereby aequorin is modified by introduction of one or more hydrazide groups into the molecule. The modification is achieved by using a particular acylating agent that is reversibly protected. Although not wishing to be bound to any particular technique, one such scheme for modifying aequorin so that it may be conjugated with an antibody and so that it retains its photolytic activity, is as follows:

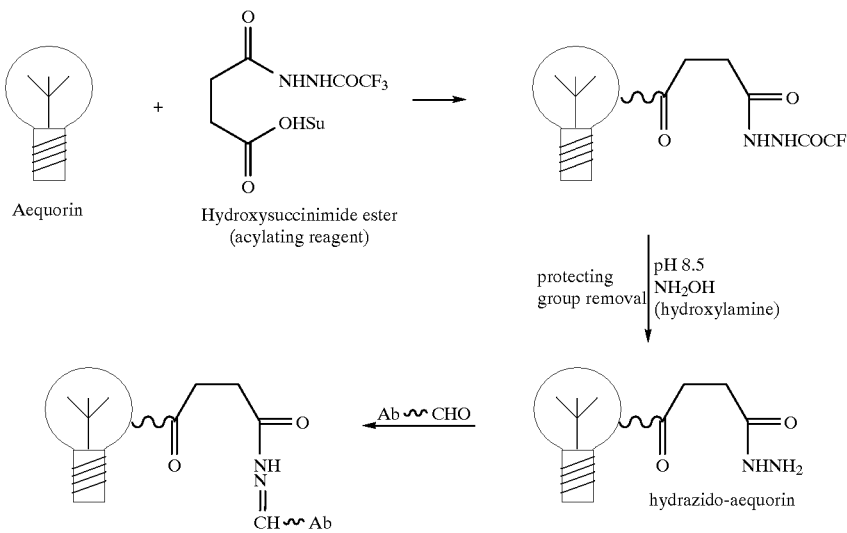

Substrate Materials

The signal generating zone, the trapping zone, and the reporter system zone can be incorporated in a wide variety of substrate materials. The primary function of the substrate materials is to act as a site or locus for the individual materials which permits the effective flow of test fluid through the device. This enables reaction between ligand and analyte, thereby permitting the signal generation mechanism to operate. The substrate can be of a variety of shapes and forms and have dimensions depending on the end use or application of the immunoassay device. In the previously noted preferred embodiment illustrated in FIG. 1A, the device has a sandwich construction of three layers. Each substrate layer typically has a thickness of at least 0.1 micron, typically greater than 1 micron, and generally in the range of about 10 to about 100 microns. Substrates can be opaque, translucent or transparent, however, the signal generated by the appropriate detection of analyte in the immunoassay device should not be masked by the nature of the substrate nor interfered with by constituents of the test fluid which may be removed at the application site opposite that of the signal generating zone.

Various materials can be employed as the substrate composition, and which are designed to avoid interfering in signal generation, passage of the test fluid, and reaction of the components. A wide variety of organic and inorganic polymers, both natural and synthetic, may be employed in each zone including polyethylene, polyvinyl chloride, polypropylene, poly-4-methylbutene, polystyrene, polymethacrylate, polyethylene terephthalate, rayon, nylon, polyvinyl butyrate, silicone films, polyformaldehyde, cellulose, cellulose acetate, nitrocellulose, etc. Other materials which may be considered include paper, glass, fiberglass, ceramics, metals, metal foils, metalloids, semiconductive materials, and others. Additionally, natural substances that can form gels or films including proteins or protein derivatives, cellulosics, drying oils, and others may be used. The support material is preferably nonswellable, and mildly hydrophilic. Other materials that may be utilized include gelatin, starch, PEG 10,000, agarose, and tape.

It is desirable to form zones or layers for the preferred embodiment device from interwoven fibers such as nitrocellulose or diazobenzyloxyme (DBM) paper. Nitrocellulose paper directly binds proteins and has been shown to be useful for immobilizing antigens. DBM matrix binds DNA, RNA, and proteins by means of covalent linkages to the diazonium group. Additionally, a porous gel such as polyacrylan agarose, or collagen can be utilized. The antigen can be trapped within the pores of the gel, or can be linked to the gel via amino groups of the ligand and carboxylic groups on the matrix. Also, particle beads containing the bound ligand trapped with cellulose or plastic fiber matrix can be employed. An example of such is polyacrylamide beads, 5–10 microns in diameter, with antigen bound to the surface with a peptide bond. The beads are trapped within a cell filter matrix having a pore size of about 1 to about 2 microns.

Details of wicking rates and light measurements from various commercially available membrane and paper materials are set forth in the accompanying examples below.

The preferred embodiment immunoassay device of the present invention may be formed by techniques described in U.S. Pat. No. 4,446,232 to Liotta, previously hereby incorporated by reference. However, the present invention includes several particularly preferred practices as follows.

The signal generating zone comprising antibodies conjugated with a signal generating label such as modified aequorin, also preferably comprises a chelating agent to remove any endogenous calcium or other metal cation contained in the biological sample to be tested which might otherwise cause premature activation of aequorin. Examples of suitable chelating agents include, but are not limited to, EDTA or EGTA. It is most preferred to chelate calcium potentially residing in the signal generating zone during one or more pretreatment steps prior to the ultimate formation of the signal generating zone. For instance, if the biological sample must be diluted prior to its application to the immunoassay device, the chelating agents could be added during that operation. EDTA could be added to the dilution buffer. Alternatively, or in addition, the chelating agent could be incorporated in, or added to, a sample collection device, such as for example a blood collection device. Specifically, an EDTA vacutainer or an EDTA coated capillary pipette could be utilized. If a wicking device is used to transport the sample to the immunoassay device, the chelating agent could be incorporated therein. Alternatively or in addition to EDTA or EGTA, an immobilized chelator is incorporated in the signal generating zone. An example of such an immobilized chelator is penta-amino tetraacetic acid. Regardless of the particular manner by which the biological sample is exposed to the chelating agent, the sample is exposed to sufficient chelating agent to prevent premature activation of the aequorin or other photoprotein by the sample.

It is also necessary that the amount of calcium or other metal cation present in the reporter system zone be sufficient to overcome any residual chelating agent. For instance, if the biological sample, e.g., serum, has 2 millimoles of calcium, and it is diluted with 10 millimoles of EDTA, then the reporter system zone should contain an excess of calcium to overcome the residual EDTA. For instance, 100 millimoles of $CaCl_2$ could be incorporated in the reporter system zone.

It will be understood that the activating agent and the photoprotein generating label are selected with respect to each other. For instance, if aequorin is utilized, then calcium is preferably employed as the activating agent. If obelin is utilized as the photoprotein, $Mn^{+2}$ can be utilized as the activating agent. With regard to $Ca^{+2}$ and $Mn^{+2}$, it may be possible to use similar metal cations as the activating agent, depending upon their reactivity with aequorin or obelin. Examples of other metal cations include for example, $Mg^{+2}$, $Ba^{+2}$ and $Sr^{+2}$.

Employing aequorin as the photoprotein, and divalent calcium as the photoprotein activating agent, the calcium is released directly by hydration of the dried reporter system zone containing the calcium salt. However, it is clear that other techniques or configurations can be used to release the calcium from the dried zone upon hydration. This includes, for example, release from a caged calcium compound. In the latter case the caged calcium compound is activated to release the calcium ions by the introduction of ultraviolet light.

It has also been discovered that the duration of light emission, that is the time period of light generation, resulting from analyte detection may be extended by impregnating the substrate forming the reporter system zone with the activating agent, e.g., calcium or caged calcium.

The amount of activating agent utilized to react with the photoprotein to thereby generate light depends on the specific device. However, for aequorin and calcium, the inventors have determined that a typical amount of $Ca^{+2}$ (in the form of $CaCl_2$) incorporated in the reporter zone is from about 10 mM to about 100 mM.

Luminometer Device

The present invention, in yet another aspect, utilizes a luminometer for sensing light emitted from the immunoassay device. The luminometer is preferably a compact photomultiplier for sensing light, utilizing an electrical power supply, and electrical circuits to quantify and display the light detected, and control the instrument. An example of a suitable luminometer is one available from Analytical Development Inc. It is preferred that the luminometer be configured to sense and measure light emitted from a surface. Artisans have described the use of a luminometer for quantitation of signals generated from a luminogenic immunoassay. See for instance, D. H. Leaback and R. Haggart, "The Use of a CCD Imaging Luminometer in the Quantitation of Luminogenic Immunoassays," *J. Bioluminescence and Chemiluminescense*, vol. 4, p. 512–522 (1989), hereby incorporated by reference.

Regardless of the specific luminometer employed in the techniques and apparatuses of the present invention, there are several preferred considerations. The immunoassay devices are preferably held or positioned by use of a holding assembly such as a test strip holder known in the art. It is also preferred that the immunoassay device be held or maintained in proper alignment with the multiplier. The holder, or the luminometer itself, should have provisions to exclude ambient light when the immunoassay device is inserted into, or otherwise engaged with the luminometer. Ambient light can be excluded from the photomultiplier in numerous ways. A sealed or sealable test strip holder can be used. The immunoassay device itself can comprise provisions to block such light or include light blocking materials in its construction. For instance, opaque materials can be utilized for non-wetted parts of the device. Light blocking, but liquid permeable materials can be utilized for wetted parts of the device. As noted, the photomultiplier may itself comprise mechanical or electronic assemblies to block or exclude ambient light. Examples of such provisions include doors, drawers, or shutters.

Image Recordation

In another aspect, the present invention also includes the use of provisions that record light emitted from the immunoassay device upon detection of analyte. Such provisions may be utilized separately or in addition to one or more photomultipliers, e.g. luminometers. A preferred example of image recordation provisions is a camera and photographic film or plates.

Figure 3:
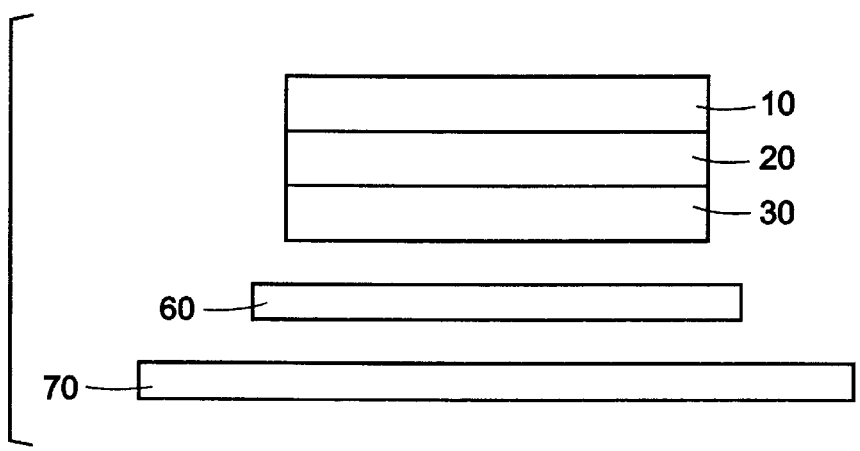
FIG. 3 is a schematic representation of the immunoassay device depicted in FIG. 1A used in combination with a shutter assembly and photographic film or plates.

In a preferred technique, an appropriate amount of photographic film or a suitably sized photographic plate is disposed proximate the reporter system zone. This is illustrated in FIG. 3. A shutter assembly 60 is positioned between the photographic film or plate 70 and the reporter system zone 30. After addition of a sample to be tested, the shutter is opened for a predetermined amount of time. The film is then developed. In such a configuration, a positive sample, i.e. the sample containing the analyte being tested for, yields a circular image. As described in greater detail below, the diameter of the circular image is proportional to the analyte concentration. This, as opposed to reflectance, is a direct indication or read of the intensity of light emission. A wide array of photographic film can be utilized. The film that is selected should have sufficient sensitivity to capture any resulting image or light generated from the immunoassay device. Two examples of suitable film speed are 20,000 ASA and 3,000 ASA.

For assays such as HCG (pregnancy), infectious agents such as streptococcus or HIV, and typical yes/no assays, the previously described film recording system is ideal. If analyte is absent in the test sample, there is no signal. In the event of a signal being produced, the film can be produced such that it contains instructions on the film surface to guide the user. For example, it is expected over the coming years that there will be an increase in home use diagnostics. In the case of a home use strep test and in the event of a positive result, the film might be manufacturer to offer the following advice, "The test is positive, please consult your physician immediately, who will prescribe a course of antibiotics for treatment of your infection."

An immunoassay device adapted for home use may also comprise a camera. With respect to the camera assembly, a single use disposable device is contemplated, which should be convenient to use and inexpensive. In this embodiment, it is preferred to use a single photographic shot contained in the camera. In order to achieve inclusion of the entire image on the film, the resultant film area would need to be about 3 inches by 3 inches. In order for the camera to be sufficiently small, a lens could be utilized to expand the image to a given dimension. The shutter could be operated as a conventional press button, which would open for approximately 1 minute and then close. The film could then be pulled or driven out in a conventional manner and developed accordingly. This device is convenient to manufacture and use, and relatively inexpensive.

In some applications, it is desirable to provide a quantitative indication of the intensity of light generated, i.e. the concentration of analyte being tested for. The present inventors contemplate several techniques for quantitive determination of light intensity.

Figure 4:
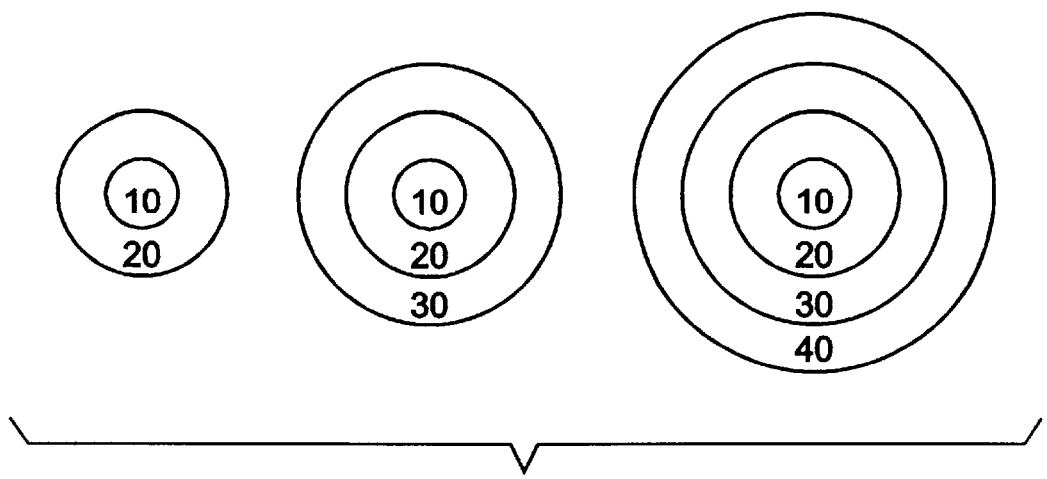
FIG. 4 illustrates a first preferred pattern for quantifying light intensity.
Figure 5:
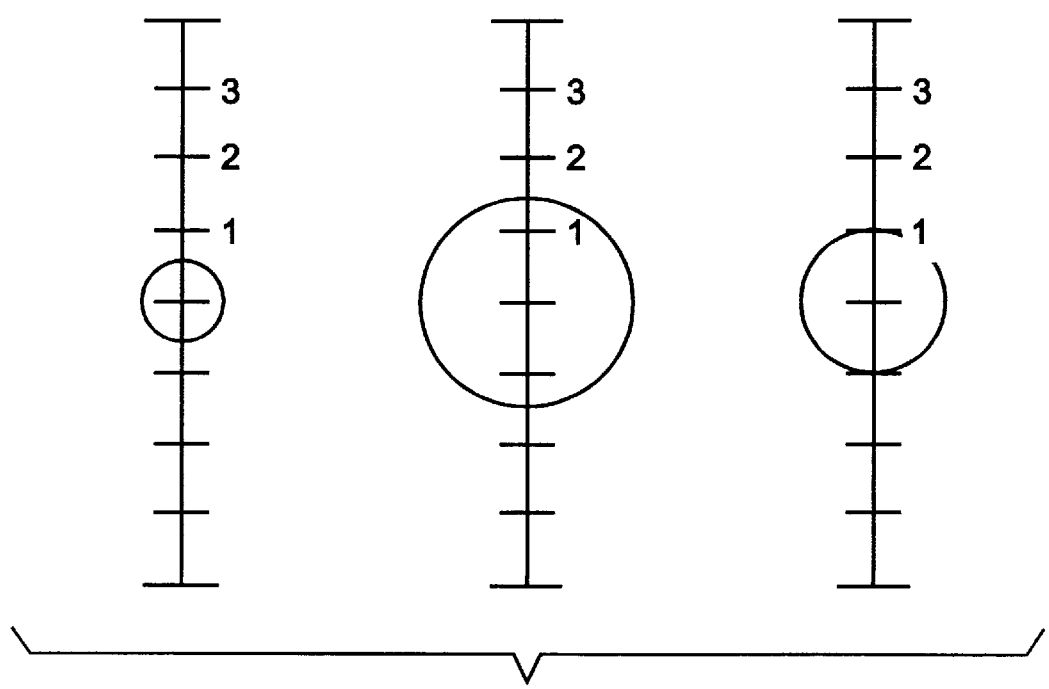
FIG. 5 illustrates a second preferred pattern for quantifying light intensity.

The area of image measurement is one possibility. Typically, the image on the film is circular for the embodiment shown in FIG. 1. Therefore the area of the image is proportional to the square of the radius. Accordingly, it is possible to build into the film surface a simple numbering system and/or pattern relating concentration of analyte to the area of the circular image. A bull's eye pattern may be used as shown in FIG. 4. Each annular region represents a particular analyte concentration level in the sample being tested. Quantitation of analyte concentration is made by identifying the annular region furthest from the center, within which the image extends. Alternatively, a bar code pattern could be used, as shown in FIG. 5.

A preferred technique for quantitative measurement is to utilize an optical scanner and appropriate software and determine a numerical value, perhaps relating to the area of the scanned image. Specifically, the image is photoscanned and relayed into a computer where appropriate software or algorithm calculates the analyte automatically and corrects for background control, if necessary.

Figure 6:
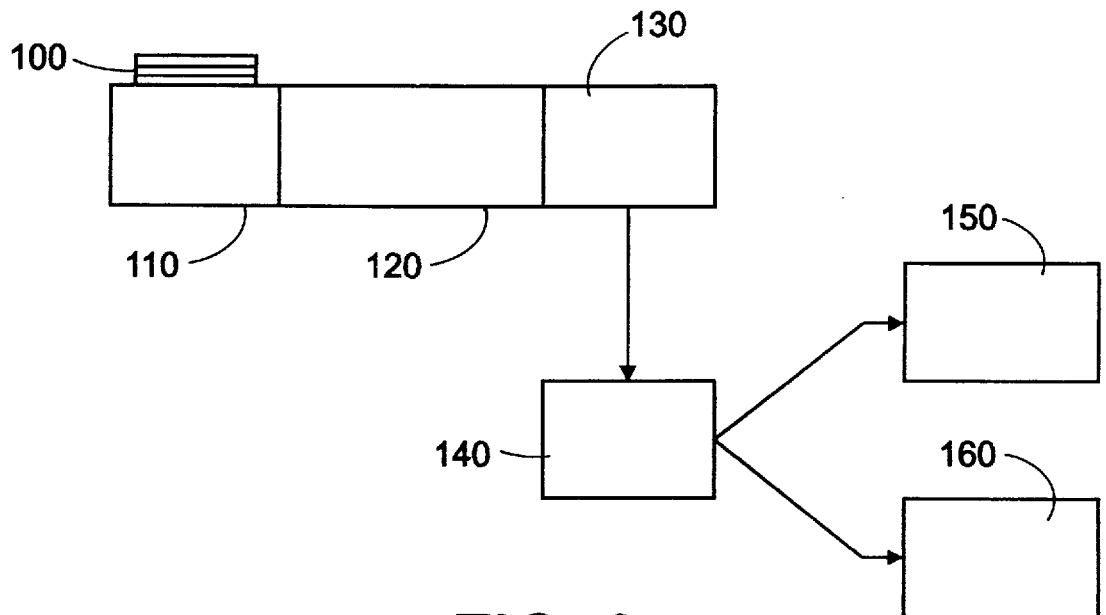
FIG. 6 is a schematic representation of an apparatus for recording, quantifying if desired, and converting an image resulting from detection of analyte by an immunoassay device, into an electronic format or computer readable form.

Furthermore, a motor driven camera may be utilized to deliver the photograph into the scanner. The scanner relays the data to the computer whereby the analysis is initiated. The information is provided immediately to a physician or technician and if necessary, can be sent to centralized records. An apparatus for conducting this analysis is shown in FIG. 6. Quantitation is conducted by calculation of pixel density or number of pixels on a CCD field contained within the image. The apparatus illustrated in FIG. 6 comprises a shutter and camera assembly 110 that, with the use of photographic film or plates, records one or more images resulting from light emitted from an immunoassay device 100. Device 100 is, for example, similar to the previously described device shown in FIG. 1. Upon exposure of the film and thus formation of an image on the film, the film is transferred to a developer unit 120. If necessary, one or more layers associated with the film may be removed or separated as known in the art. Upon development, the film and image are scanned, preferably by an optical scanner 130, to produce an electronic file or representation of the image. The scanned image is then forwarded to a computer 140 which performs a wide array of functions if needed, with respect to the scanned image. The scanned image, or a modified version thereof, can then be sent to a central file 150 or to a printer 160.

In yet another embodiment, recordation and measurement of light signals can be made without the use of film. Digital cameras are contemplated. They are becoming less expensive as of recent. Such cameras eliminate the problems and cost associated with film development. These cameras typically hold up to 20 images and most importantly, they download to a computer directly and so eliminate the need for scanning an image.

The above described systems are designed primarily as single read situations, i.e. one patient sample/run. However, there are situations where time is not critical and multiple readings are preferred. A standard 96 well plate format (ELISA) could be modified to utilize the techniques of the present invention.

Millipore Multi-Assay™ plates are particularly well suited for modification in accordance with the present invention. These plates are constructed in such a manner that the plastic bottom of the well can be replaced by a porous membrane. Although Millipore produces a number of different plates of alternate membranes, the membrane of immediate interest is the Glass Fibre format. The glass fibre well bottoms allow passage of liquid by wicking. Other formats require vacuum filtration. Other attractive features of the glass fibre matrix are: (i) the matrix binds protein tenaciously through non-covalent interaction (Lewis acid type); (ii) the fibers can be silanized and further modified to allow covalent binding of small ligands when required; and (iii) they have a reasonably large surface area. An example of this embodiment in the form of a testosterone assay is as follows. A Millipore glass fibre is utilized.

Figure 7:
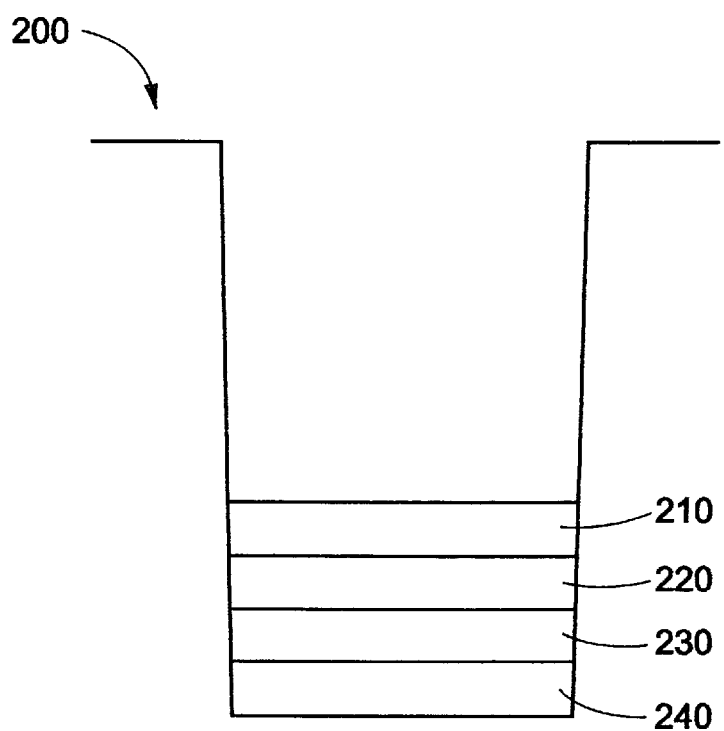
FIG. 7 is a schematic representation of a modified glass fibre well bottom, which after modification, comprises an alternate preferred embodiment immunoassay device.

The glass fibre well bottom corresponds to the trapping zone. The 96 well plate comprises a series of control wells, standard curve wells, and test wells. The light signal is generated by horseradish peroxidase/$H_2O_2$/luminol. The emitted light is captured on 20,000 ASA film. The data is generated by photo scanning and computer analysis. The modified glass fibre is illustrated in FIG. 7. Disposed at the bottom of the glass fibre well are a plurality of layers or zones as follows. A signal generating zone 210 comprises mouse alpha-testosterone and HRP conjugate maintained in 3IET paper. A trapping zone 220 is formed from glass fiber containing immobilized BSA-testosterone is positioned directly under the signal generating zone 210. A lower- or bottom-most reporter system zone 240 is positioned in the well bottom. The reporter system zone 240 comprises a transparent layer of luminol and urea peroxide. An intermediate wick layer 230 is disposed between the trapping zone 220 and the reporter system zone 240. Quantitation can be achieved as previously described.

Figure 8A:
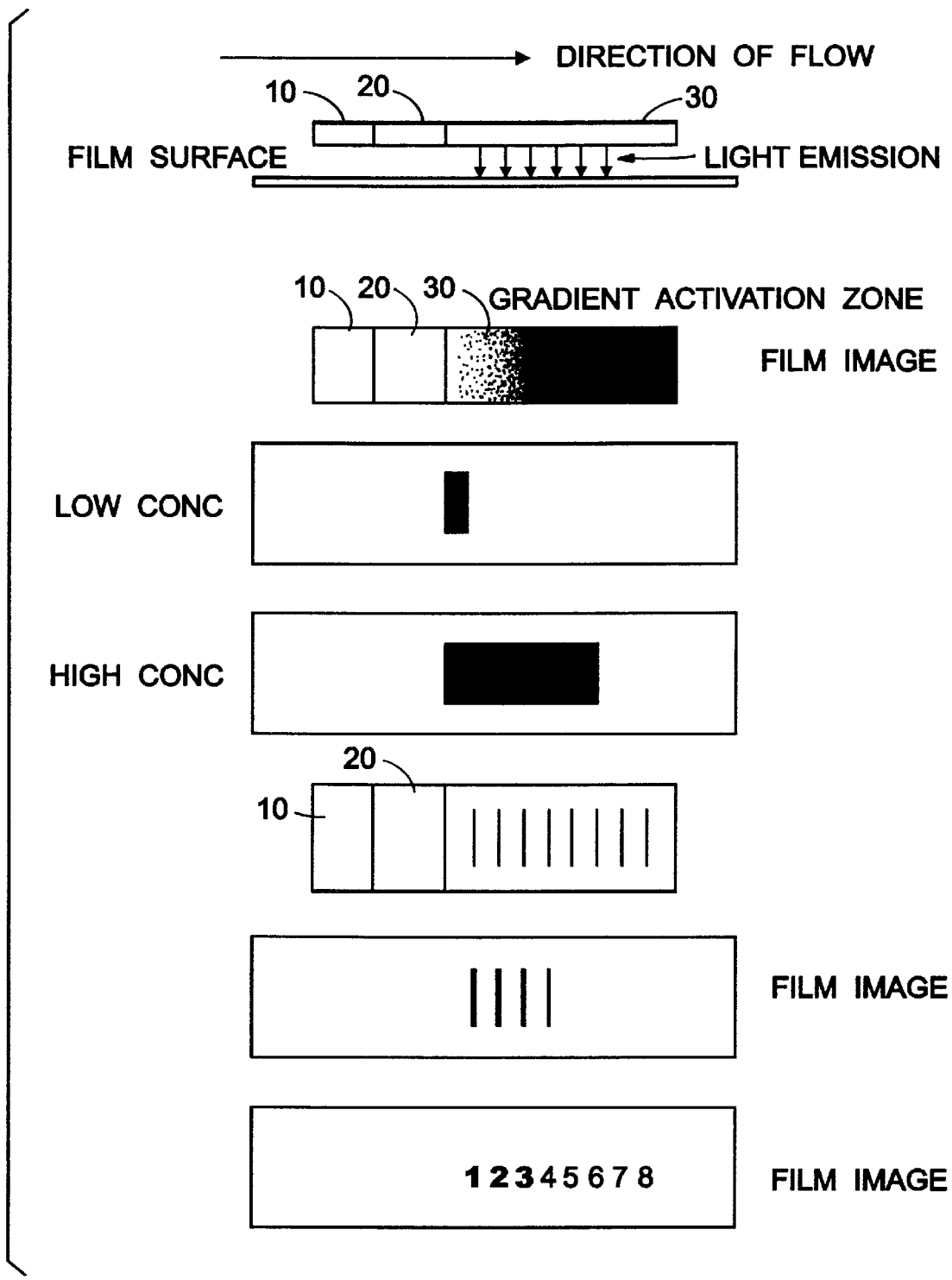
FIG. 8A illustrates an alternate arrangement for the various component zones in a preferred embodiment immunoassay device, and further illustrates representative images and patterns for quantifying analyte concentration.
Figure 8B:
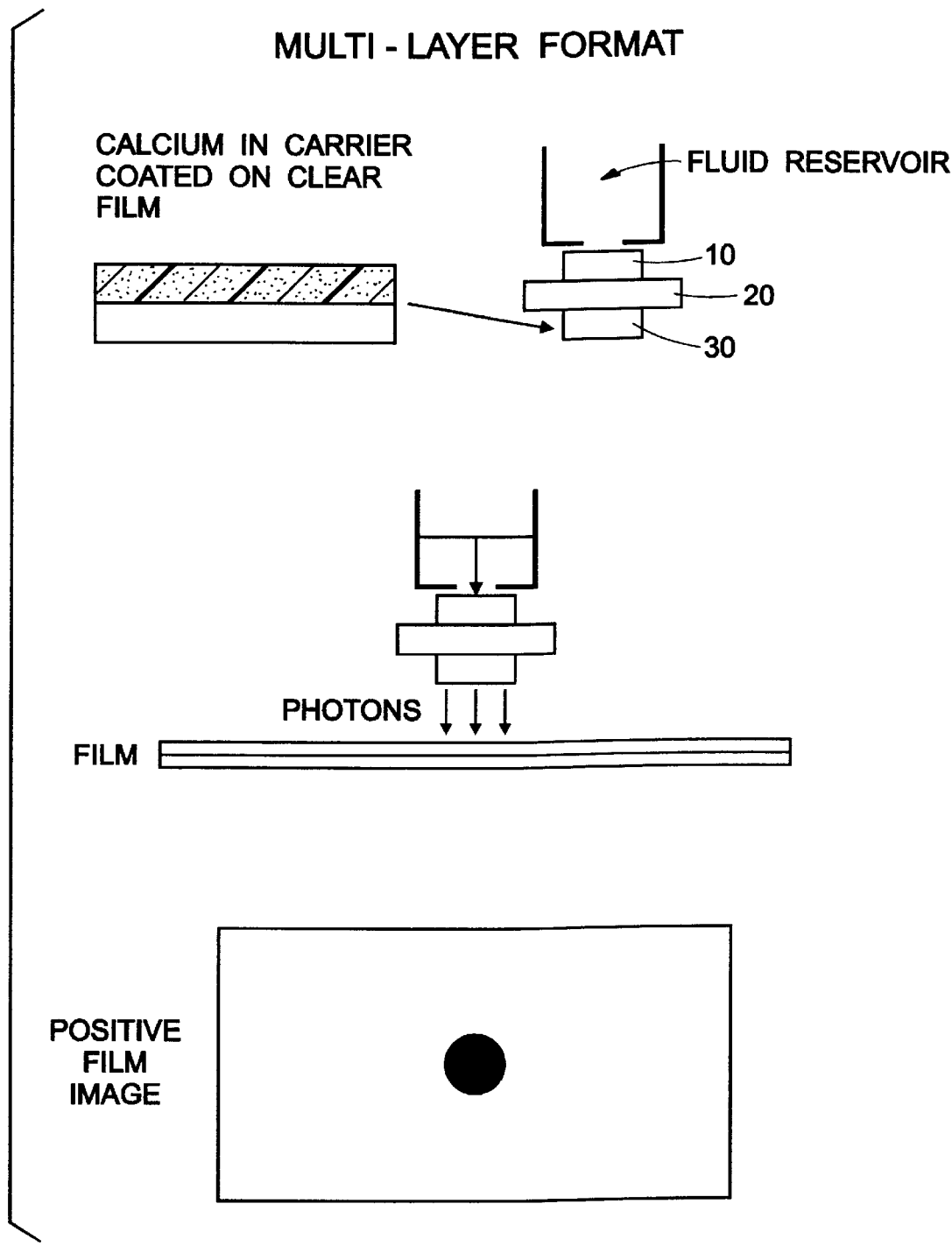
FIG. 8B is another alternate embodiment of a preferred apparatus for recording a light image from an immunoassay device.

The previously described three layers of the preferred embodiment immunoassay device can be arranged in a variety of fashions. In one such arrangement, the signal generating zone 10, the trapping zone 20, and the reporter zone 30 are all disposed in a common plane. This configuration is illustrated in FIG. 8A. In this embodiment, a test sample is applied to the end of the collection of zones at which is located the signal generating zone 10. Accordingly, the test sample serially diffuses into the trapping zone 20 and then the reporter system zone 30. In the event that photographic film is utilized to record any resulting image, the image, and specifically, the length of the image, is proportional to the concentration of the analyte in the test sample for which testing is conducted.

Figure 8C:
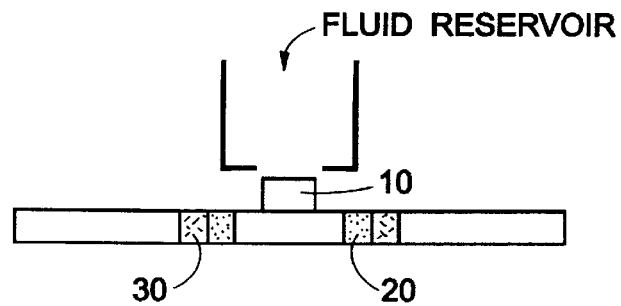
FIG. 8C is another alternate embodiment of a preferred apparatus for recording a light image from an immunoassay device.
Figure 8C:
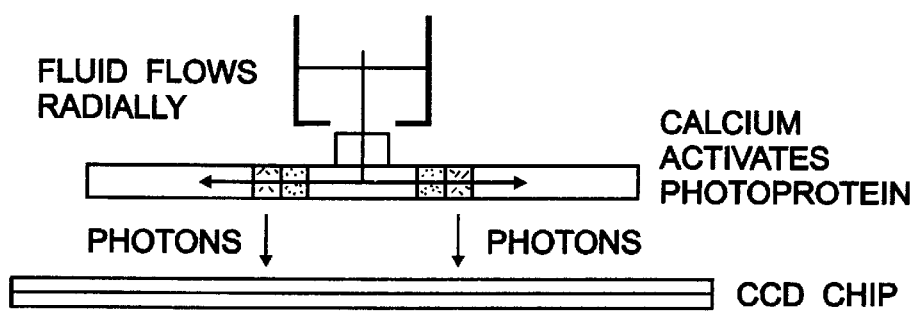
Figure 8C:
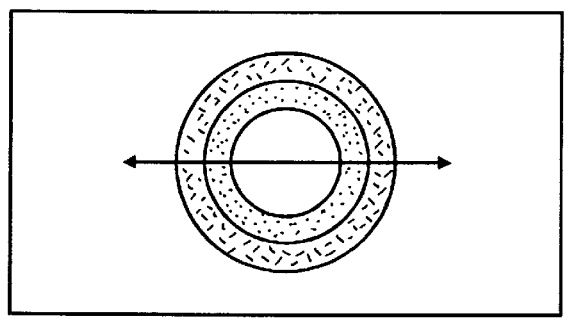
Figure 8C:
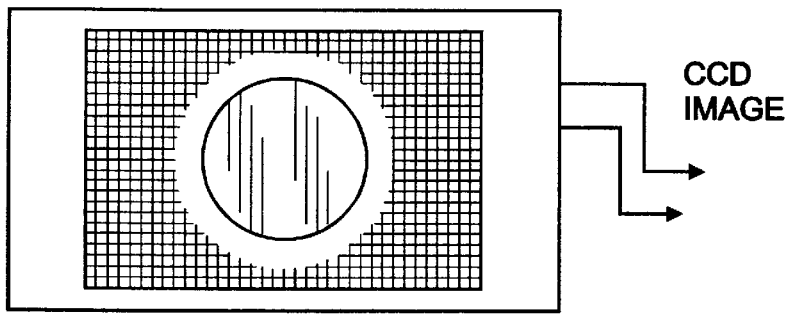
Figure 8D:
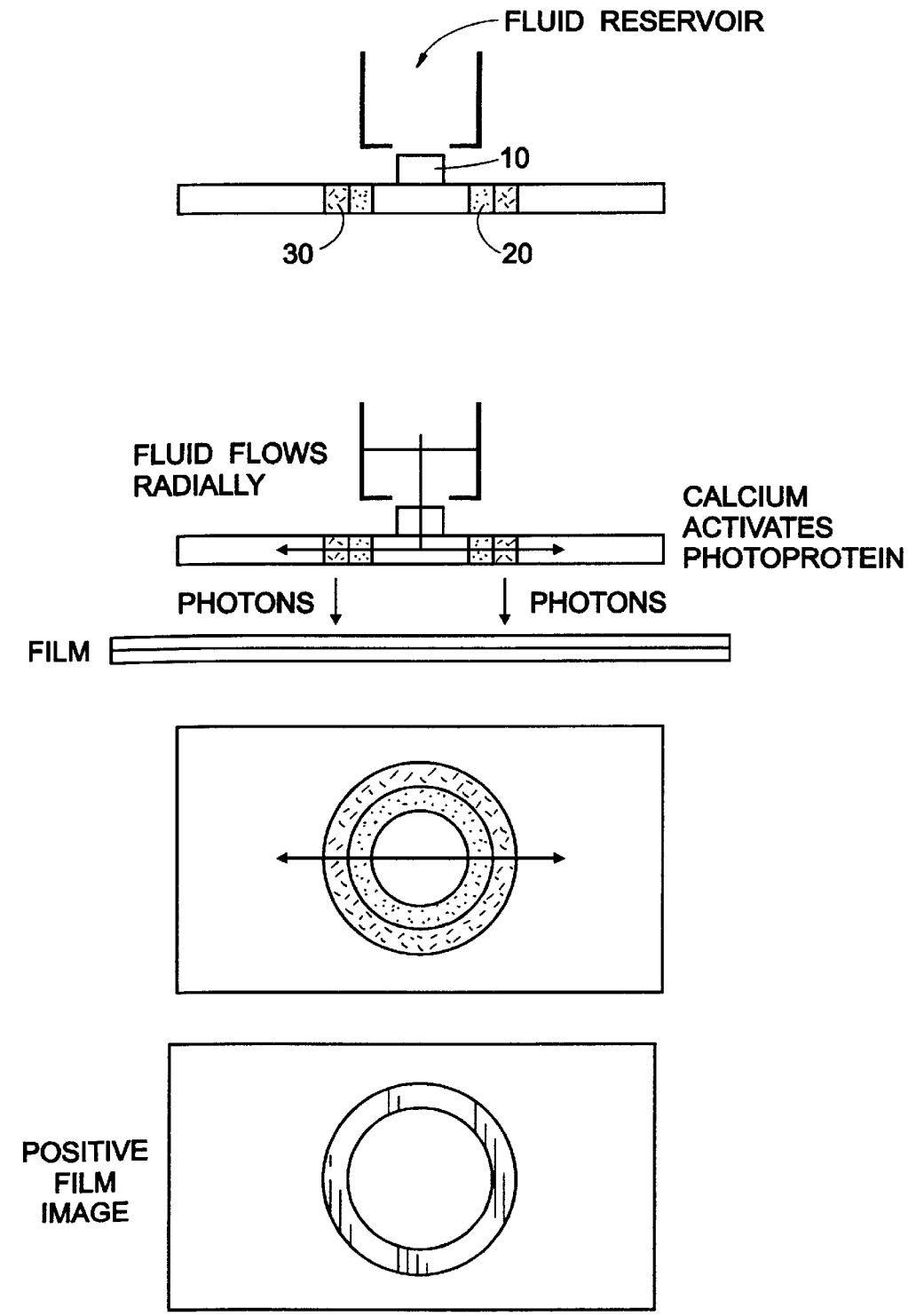
FIG. 8D is another alternate embodiment of a preferred apparatus for recording a light image from an immunoassay device.
Figure 8E:
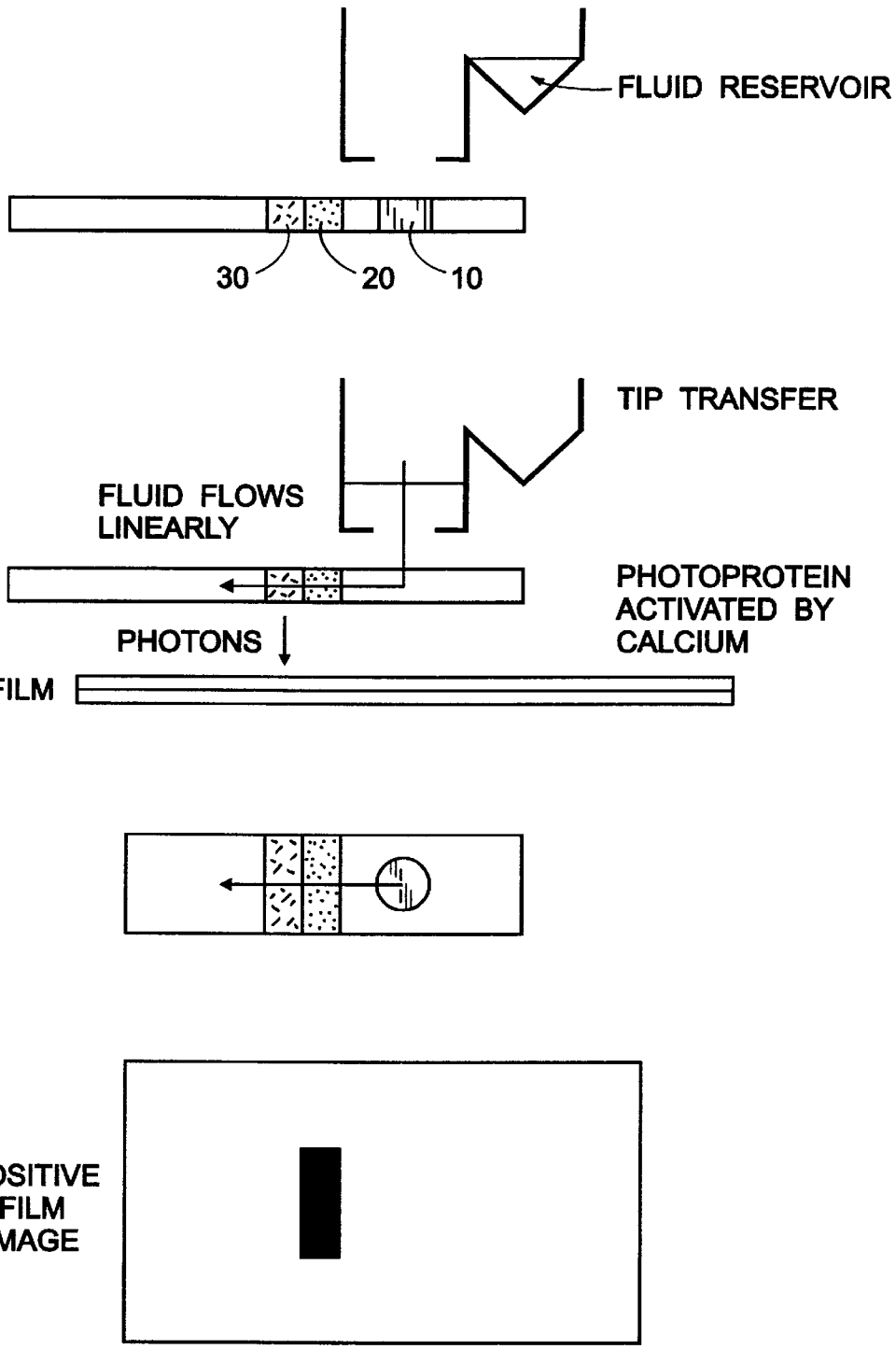
FIG. 8E is another alternate embodiment of a preferred apparatus for recording a light image from an immunoassay device.
Figure 8F:
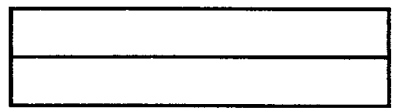
FIG. 8F is another alternate embodiment of a preferred apparatus for recording a light image from an immunoassay device.
Figure 8F:
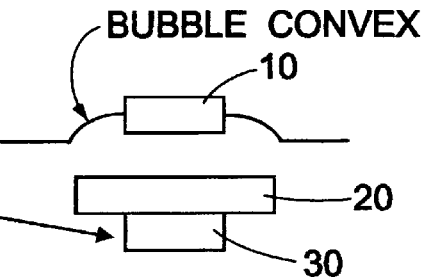
Figure 8F:
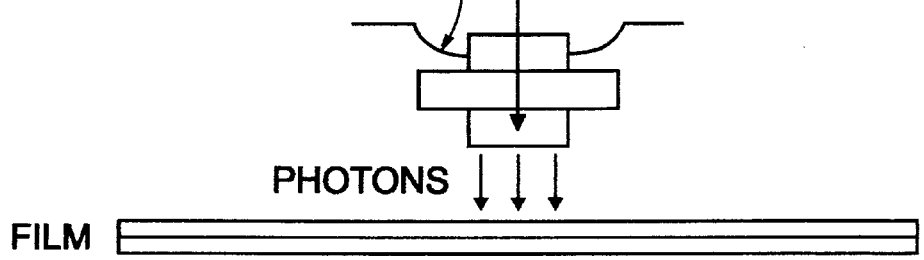
Figure 8F:
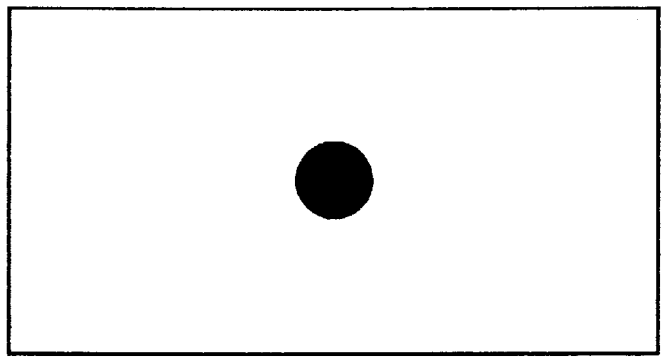

The present invention provides other embodiments of apparatuses for recording or otherwise capturing a light image from an immunoassay device. FIGS. 8B–8F all illustrate schematically, examples of such apparatuses. In all figures, the signal generating zone, the trapping zone, and the reporter system zone are designated as 10, 20, and 30 respectively. The apparatus of FIG. 8F employs a bubble format which, when depressed or inverted, forms a depression to initiate the flow from the signal generating zone 10 to the trapping zone 20. It will also be noted that the zones 10, 20, and 30 of the immunoassay device can be arranged or oriented in a variety of ways. FIGS. 8C and 8D illustrate a centrally located zone 10 and annular zones 20 and 30. FIG. 8E denotes linearly and serially arranged zones 10, 20, and 30.

In the preferred embodiment immunoassay devices, the signal generating zone preferably comprises: 25 mM Hepes pH 7.4, 100 mM $MnCl_2$, 0.5% Glucose, 0.5% Mannitol, 0.005% Peg-40, and 150 mM EDTA. The trapping zone may comprise digoxin-BSA, as described in the accompanying examples set forth below. The reporter system zone may be in the form of a solid permeable woven matrix, a porous substance, a dried film, or a dried coating on a transparent surface. The reporter system zone can be coated on the surface of photographic film, a photomultiplier transducer, or a light sensing photodiode, or CCD. If the reporter system utilizes calcium, a calcium gel may be prepared as described in the examples, and deposited on a suitable substrate. The reporter system can also produce a color reaction such that two or more different analytes can be measured simultaneously, one by light and one by color.

As described herein, the present invention can be incorporated into a three zone layered diagnostic device employing a flow-through trapping zone according to U.S. Pat. No. 4,446,232 to Liotta, previously hereby incorporated by reference. The result is a highly sensitive and rapid diagnostic light based assay. Moreover, the manner, timing, and local concentration of the dried or caged calcium or other immobilized activating agent can extend the length of the light pulse and provides a technique for performing multiple assays at once, distinguishing different ligands, and geometrically altering the location of light emission. This can provide a means to produce a pattern of photographic recording which shows geometrically the concentration of the diagnostic analyte.

The present invention remarkably provides a rapid dry layered diagnostic immunoassay requiring no washing steps and no addition of reagents. The assay can be completed in a short period of time, typically less than 30 seconds. The assay achieves analyte sensitivities in the picomolar or better range. Sensitivities of $10^{-17}$ or better have been achieved. The assays provide a readily detectable light signal, the duration of which is extended due to the technique by which the activating agent, e.g., calcium, is incorporated into the reporter system zone.

EXAMPLES

Three Layered Dry Phase Immunoassay Device

A light emitting immunoassay device in accordance with the present invention was prepared as follows. The device was configured to test for the presence of theophylline in a liquid sample. A dry conjugate of antibody conjugated with horseradish peroxidase (HRP) was added to a solution of 25 mM Hepes, 0.5% glucose, 0.5% manitol, 0.05% PEG, 0.05% Tween-20, and 1% RaT. The resulting mixture was added to a thin planar substrate to form a signal generating layer. A trapping zone was formed by incorporating theophylline.BSA on Gelman. A third layer, the reporter system zone, was prepared by impregnating a thin layer substrate with a solution of MeOH, 1.5mM luminol, 10 mM of 4-iodo-phenol, and 0.8% AOT-100.

Test samples containing varying amounts of theophylline in water were prepared. Each test sample contained 0.003% $H_2O_2$.

Figure 9A:
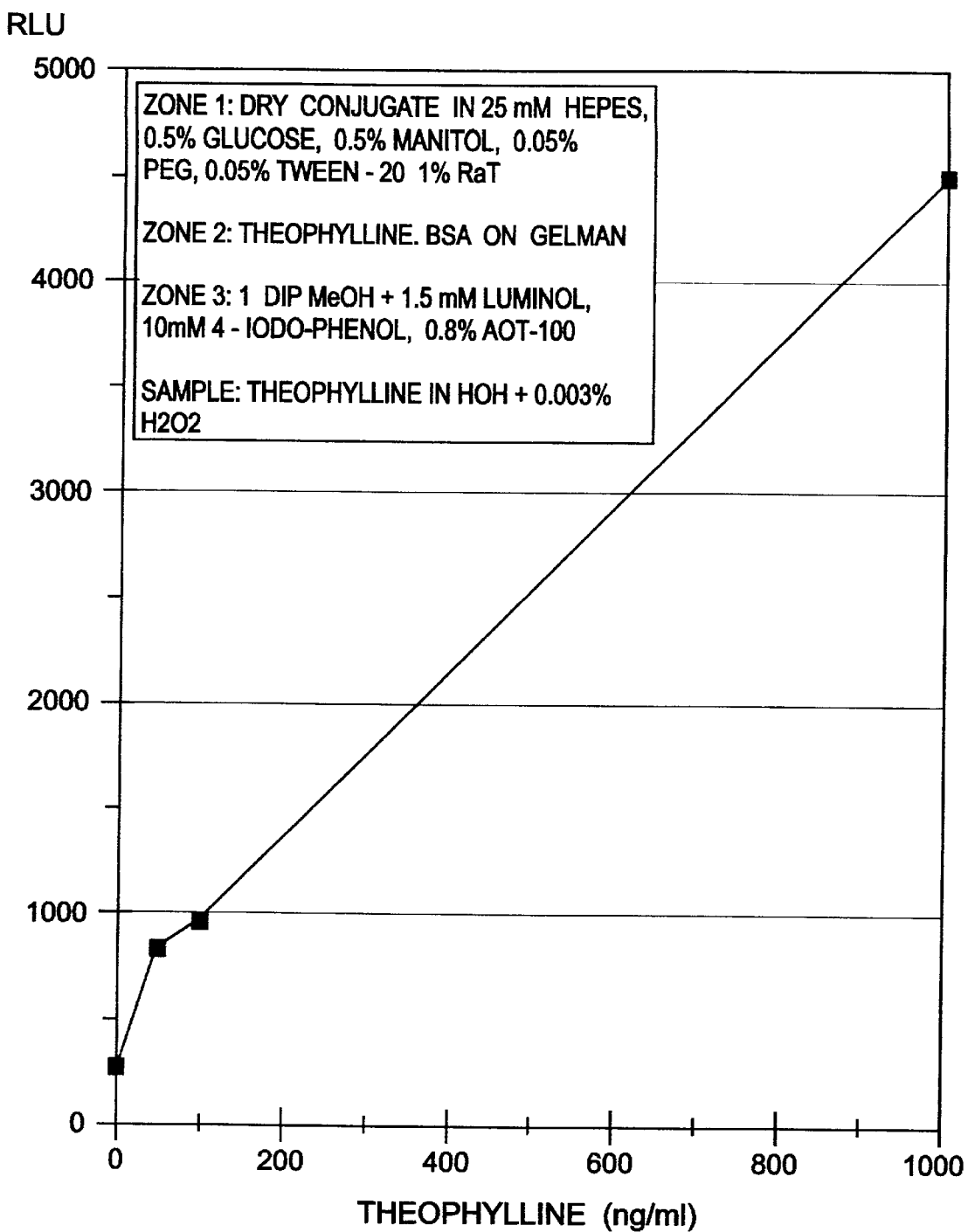
FIG. 9A is a graph of testing results in which the concentration of an analyte, i.e., theophylline, was determined using an immunoassay device in accordance with the present invention.

Each test sample was administered to an immunoassay device as previously described, and specifically, to the signal generating zone. A light measuring instrument was employed to measure the amount of light in RLU's generated from the reporter system zone in each device. The results of this testing are presented graphically in FIG. 9A.

Antibody Modification The following technique is utilized for antibody-HRP conjugation using PDP hydrazide. The following reagents or solutions were utilized:

Labeling Solution: 0.1M NaAc pH 5.5 (100 ml; NaAc 1.36 g; Acetic acid to pH)
Conjugation Buffer: 0.1M NaPi, 5mM EDTA pH 6.0 (200ml; Mono NaPi 2.42 g; Di NaPi.35 g; EDTA.37 g; NaOH to pH)
NaPeriodate Solution: b 0.1M NaPer in Labeling Solution (0.47 ml; 10 mg NaPeriodate)
PDP-Hydrazide: 20 mM PDP-Hydrazide (2.2 ml DMSO; 10 mg PDP-Hydrazide)
2-MEA, HCL (6 mg)
Desalting column
Cetricon 30
HPLC Buffer
Abx Buffers The procedure is as follows.

A. Prepare antibody for labeling
 1. Exchange antibody into labeling solution. Antibody concentration should be 2 mg/ml final. This can be accomplished with a desalting column or a Centricon 30. The reaction volume should be one ml.
 2. Measure and record $A_{280}$ and volume of antibody.
 3. Run HPLC to determine unlabeled profile and retention time.
 4. Chill in ice bath B. Add sodium meta-periodate
 1. Add 0.1 ml of chilled 100 mM sodium meta-periodate to 1 ml antibody solution.
 2. Chill in ice bath 20 minutes in the dark.

C. Stop reaction with glycerol
 1. Add 1.2 µl of glycerol to reaction for a final concentration of 15 mM
 2. Chill in ice bath 5 minutes in the dark D. Exchange into labeling solution
 1. Exchange reaction into labeling solution using desalting column.
 2. Concentrate reaction to 1 ml using Centricon 30

E. Add PDP-hydrazide to sample
 1. Add 325 µl of 20 mM PDP-hydrazide stock to 1 ml reaction volume.
 2. Agitate 2 hours RT in the dark F. Exchange into conjugation solution
 1. Exchange reaction into conjugation solution using desalting column.
 2. Concentrate reaction to 1 ml using Centricon 30

G. Add 2 MEA.HCL
 1. Add 6 mg of 2ME-A to 1 ml reaction volume.
 2. Incubate 90 minutes at 37° C.

H. Exchange into conjugation solution
 1. Exchange reaction into conjugation solution using desalting column.

I. Add M-HRP
 1. Add 5 mg of Mal-HRP to reaction mixture.
 2. Conjugate overnight at 4° C.

Although not wishing to be bound to any particular reaction scheme, the foregoing methodology primarily involves the following chemistry. Aldehyde groups are created on the antibody by reaction with periodate. The aldehyde groups react with the hydrazine group on the PDP-hydrazide to form a hydrazone. Mercaptoethylamine selectively cleaves the disulphide bridge in the PDP-hydrazide to expose a thiol function. The thiol function, which is located in the carbohydrate region of the antibody, is reacted with maleimido HRP to create the conjugate.

Conjugation of Monovalent Antibody Fragments

A. General Outline
  1. Exchange antibody into digestion buffer TRIS, cystein, EDTA
  2. Add immobilized Ficin beads to Ab
  3. Monitor digestion with HPLC
  4. Separate Ficin beads and Ab to stop reaction
  5. Add BME to 25 mM final to reduce (Fab')$_2$
  6. Monitor reduction on HPLC
  7. Stop reduction by exchanging into conjugate buffer
  8. Add M-photoprotein and conjugate overnight
  9. Clean up on Abx column B. Reagents
  1. Immobilized Ficin (SIGMA) 25 units, reconstitute in 2.0 ml of dH$_2$O
  2. (100 ml) Digest Buffer 50 mM TRIS pH 7.0, 1 mMcystein, 5 mM EDTA buffer
  3. 3× Digest Buffer 150mM TRIS pH 7.0 3 mMcystein, 15 mM EDTA (for dilution)
  5. (100 ml) Conjugation Buffer 0.1 M NaPi, 5 mM EDTA, pH 6.0
  6. BME 0.2 M in Digest Buffer (140 µl in 10 ml.)
  7. desalting column
  8. Abx buffers
  9. Centricon 50

C. Prepare Antibody for Digestion
  1. Exchange Antibody into 50 mM TRIS pH 7.0, 1 mM Cystein, 5 MM EDTA. Antibody concentration should be 2 mg/ml final. This can be accomplished by desalting column, Centricon 50, or by dilution with 3× digestion buffer if antibody is >6mg/ml.
  2. Measure and record A$_{280}$ and volume of Ab.
  3. Run HPLC to determine undigested profile and retention time.

D. Add Immobiled Ficin
  1. Put 2.5 units per mg of IgG digested of immobilized Ficin into a glass tube.
  2. Wash with TRIS pH 7.0, Cystein, EDTA buffer twice by centrifuging and resuspending in buffer. Leave beads in minimum volume.
  3. Add Ab to washed beads and plate at 37° C. on shaker.

E. Monitor Digestion
  1. Monitor digestion with HPLC. The first time point should be 15 to 30 minutes.
  2. Expect digestion to proceed rapidly and then nearly stop at 25% to 80% digested.
  3. Stop digestion when rate slows, usually 30 to 120 minutes.
  4. Stop digestion by centrifuging out beads with mini column.

F. Reduce (Fab')$_2$
  1. Measure and record the volume and A$_{280}$ of the digest.
  2. Add BME to 25 mM final BME.
  3. Monitor reduction with HPLC. The first time point should be 15 minutes. Reduction should proceed very quickly.
  4. Stop reduction by exchanging into conjugation buffer. Two passes on a desalting column are sufficient. NOTE: It is critical that the cystein be removed or it will react with the M-HRP.

G. Conjugate to Photoprotein Aequorin
  1. Measure and record the volume and A$_{280}$ of the digest.
  2. Add M aequorin photoprotein to at least 2:1 w/w/ ratio.
  3. Conjugate O/N @ 4° C.

H. Ficin Conjugation Procedure
  1. Exchange into 0.1 M NaPl, 1.0 mM cystein, pH 7.0. Or dilute with 3× digestion buffer if >6 mg/ml.
  2. Add immobilized Ficin and incubate at 37° C. 1–2 hr.
  3. Separate Ficin from Ab, dilute 1:3 in SPA binding buffer, run over SPA column. Or skip SPA column if digestion is >85%.
  4. Add BME and incubate at 37° C. Monitor reduction with SEC-HPLC.
  5. Run over G-25 to remove BME (twice)
  6. Add M-photoprotein and allow to conjugate overnight at 4° C.
  7. Purify on ABx.

Trapping Zone

Synthesis of Digoxin-BSA

A. Oxidation of Digoxin
  1. Dissolve 436 mg Digoxin in 20 ml absolute ethanol.
  2. Add 20 ml 0.1M sodium periodate in distilled H$_2$O.
  3. Incubate for 25 min. at room temperature.
  4. Add 0.6 ml 1M ethylene glycol.

B. conjugation of Digoxin to BSA
  1. Dissolve 560 mg DSA in 20 ml dH$_2$O.
  2. Prepare 5% K$_2$CO$_3$.
  3. Set-up pH meter with stir plate and stir BSA.
  4. Begin dropwise addition of Oxidized Digoxin to the BSA, maintaining pH 9.0–9.5 with the 5% K$_2$CO$_3$.
  5. Incubate for 45 min. at room temperature.

C. Reduction
  1. With stirring, add 20 ml. of 1.5% Sodium Borohydride in dH$_2$O.
  2. Incubate for 3 hr. at room temperature with stirring.
  3. Reduce pH to 6.5 with dropwise addition on 1 M formic acid.
  4. Incubate at room temperature for 1 hr. with stirring.
  5. pH to 8.5 with 1 M NaOH.
  6. Dialyze overnight against water.

D. Purification
  1. pH to 4.5 with 1 M HCL.
  2. Incubate for 1 hr. at room temperature.
  3. Incubate at 4° C. for 4 hr.
  4. Centrifuge at 1000 g for 1 hr. Discard supernate.
  5. Resuspend in 5 ml 0.15 M NaHCO$_3$.
  6. Exhaustively dialyze against water.
  7. Lyophilize and store at −20° C.

Trapping Layer

1. Incubate a 3"×3" piece of Gelman SV-450 in 10 ml of 2 mg/ml Digoxin-BSA (IMX digoxim-BSA method)in 0.1 M NaPi, pH 7.2, for 30 minutes on shaker.
2. Block with 1% Non-fat dry milk in 0.1 M NaPi, pH 7.2, for 20 minutes on shaker.

3. Wash 4 times in dH20 for 5 minutes on shaker.
4. Dry at 75° C. for 15 min.

Activation Reporter System Zone

Figure 9B:
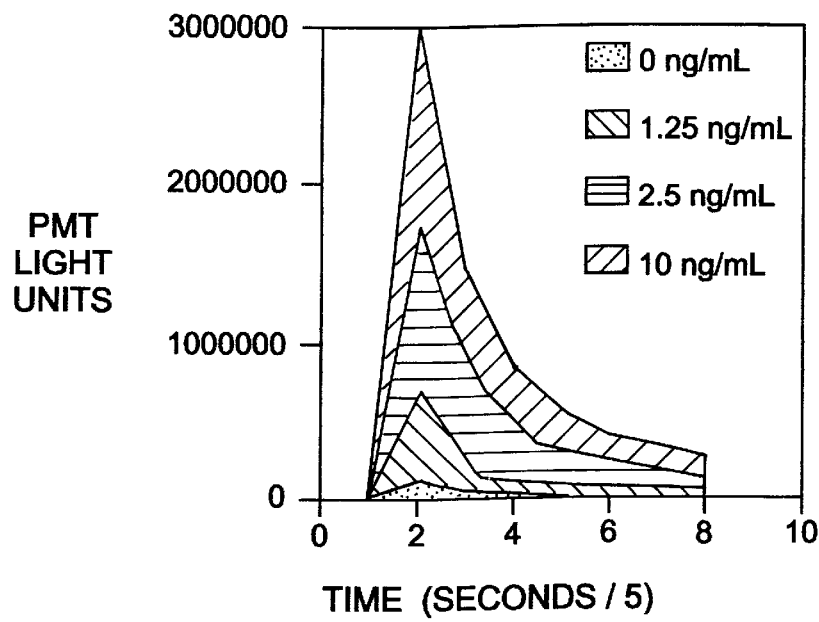
FIG. 9B illustrates testing results in which the concentration of digoxin was determined using a dry immunoassay device with a calcium activation zone and an aequorin conjugate, the testing results including film recording and luminometry measurements.
Figure 9B:
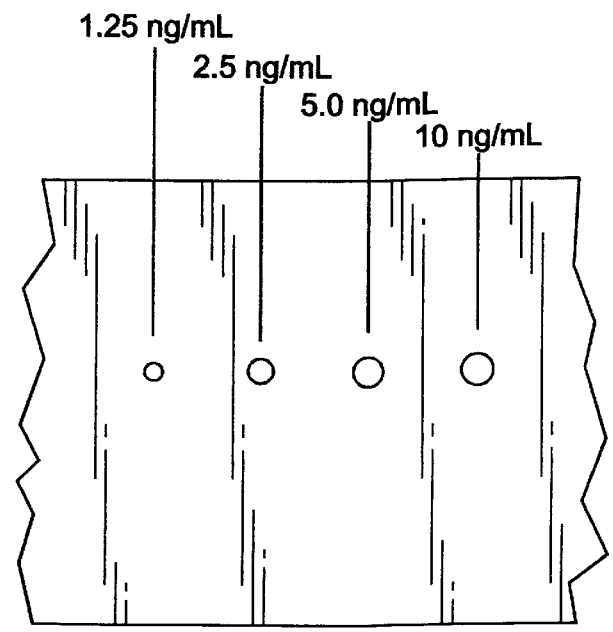

Calcium Gel formulation for use with Aequorin Conjugates
1. Make 100 mM Tris buffer pH-8.5 containing 0.1% Sodium Azide (preservative)
2. Take 100 ml of Tris buffer and add 1.47 grams of $CaCl_2$ (100 mM)
3. To this solution add 1–10% (w/v) Gelatin from Bovine skin (Also use Poly Vinyl Alcohol)
4. Heat at 37 degrees Celsius in a water bath for 30 minutes
5. Gel can now be spread and/or dried FIG. 9B illustrates the results of testing in which the concentration of digoxin was determined using a dry immunoassay device with a calcium activation zone and an aequorin conjugate. FIG. 9B illustrates luminometry measurements and film recording.

Substrate Materials for Assay System

Membrane/paper from Gelman received; Absorbent Paper 111 and 113; A/E Glass Fiber Filter Paper; Cytosep; and Transorb. Their wicking capabilities for use with the surface luminometer and ability to quench the light were tested. The various papers were cut into four different wick lengths: 4.5 cm, 4 cm, 3 cm, and 2 cm. Porex and A/E Glass Fiber paper were treated with 1 mg/mL BSA in an effort to limit their protein binding capacities. By using a reflectometer, wicking times of the various membranes/papers were determined. Results: Porex either treated or untreated has the shortest wicking time at approximately 3 seconds for every 2 cm. A/E Glass Fiber Filter paper has the longest wicking time at around 30 seconds for every 2 cm. The results of this testing are illustrated in FIG. 10.

Aequorin Conjugate Stabilization for Signal Generating Zone (Zone 1) TSH Assay Aequorin buffer was prepared as follows: 50 mm Hepes, 1 mm Kcl, 10 mm EGTA (pH 8.0), 10 mm $MgCl_2$, and 0.1% azide. The following carrier proteins were tested: 1% casein in PBS, Seablock (from Pierce Chemicals), 5% Blotto in PBS, and 1% Blotto in PBS. Aequorin anti-TSH was diluted 1/500 in aequorin buffer.

Results indicated that the maximum RLU/30 seconds light units for 10 microliters of aequorin IgG (conjugate) was 91,000. 10 microliters of conjugate combined with 20 microliters of Seablock yielded 99,000 units compared to only 3000 for casein and 500 for 5% Blotto. 1% Blotto yielded 75,000. Thus, Seablock preserved full functional activity.

The invention hpts been described with reference to several preferred embodiments. Obviously, modifications and alterations will occur to others upon a reading and understanding of this specification. It is intended to include all such modifications and alterations insofar as they come within the scope of the appended claims or the equivalents thereof.

One particularly preferred alternate embodiment or modification involves switching or replacing components or agents in one zone with others in another zone. For example, the present invention includes an embodiment of a testing device and related methods that detect, and measure the quantity of, antibodies in a liquid test sample. In that embodiment, analyte or antigen that is linked or conjugated with a signal generating label or photoprotein is provided in the signal generating zone. Accordingly, immobilized or bound antibody, corresponding to the antibody being tested for, is retained within the trapping zone.

Having thus described the invention, it is claimed:

1. A method for activating light emission by a photoprotein adapted for use in a diagnostic assay, said method comprising:

providing a substrate having a zone coated or impregnated with at least one of a dried salt of a metal cation and a dried caged metal cation compound to produce a dried metal cation zone;

allowing a liquid comprising a photoprotein labeled reagent to contact said dried metal cation zone; and releasing metal cation from said dried metal cation zone to activate said photoprotein labeled reagent, thereby resulting in light emission.

2. The method of claim 1 wherein said metal cation is selected from the group consisting of $Ca^{+2}$, $Mn^{+2}$, $Mg^{+2}$, $Ba^{+2}$, $Sr^{+2}$, and combinations thereof.

3. The method of claim 2 wherein said metal cation is $Ca^{+2}$.

4. The method of claim 1 wherein said photoprotein labeled reagent comprises a photoprotein selected from the group consisting of aequorin, obelin, mitrocomin, clytin, and combinations thereof.

5. The method of claim 4 wherein said photoprotein is aequorin.

6. A method for activating light emission by a signal generating label adapted for use in a diagnostic assay, said method comprising:

providing a first substrate containing. a dried signal generating labeled reagent comprising peroxidase;

providing a second substrate containing luminol, said second substrate proximate to said first substrate;

hydrating said first substrate thereby releasing said signal generating labeled reagent from said first substrate; and allowing said signal generating labeled reagent to contact said second substrate whereby said peroxidase reacts with said luminol and emits light.

7. The method of claim 6 wherein said peroxidase is horseradish peroxidase.

8. A diagnostic device adapted for producing a visual indication of analyte concentration, said device comprising:

a first substrate or region thereof, comprising signal generating labeled ligand;

a second substrate or region thereof proximate to said first substrate, said second substrate comprising immobilized analyte adapted for binding said signal generating labeled ligand; and a third substrate or region thereof proximate to said second substrate, wherein said second substrate is disposed between said first substrate and said third substrate, said third substrate comprising an activating agent capable of reacting with said signal generating labeled ligand and thereby emitting light from said third substrate.

9. The diagnostic device of claim 8 wherein said signal generating labeled ligand comprise ligands conjugated with a signal generating label selected from the group consisting of photoproteins and peroxidase agents.

10. The diagnostic device of claim 9 wherein said photoproteins is selected from the group consisting of aequorin, obelin, mitrocomin, clytin, and combinations thereof.

11. The diagnostic device of claim 10 wherein said photoprotein is aequorin.

12. The diagnostic device of claim 10 wherein said activating agent is one or more metal cations.

13. The diagnostic device of claim 12 wherein said metal cations are selected from the group consisting of $Ca^{+2}$, $Mn^{+2}$, $Mg^{+2}$, $Ba^{+2}$, $Sr^{+2}$, and combinations thereof.

14. The diagnostic device of claim 13 wherein said metal cation is $Ca^{+2}$.

15. The diagnostic device of claim 9 wherein said peroxidase agent is horseradish peroxidase.

16. An apparatus for quantifying analyte concentration in a liquid test sample, said apparatus comprising:
- a diagnostic device adapted for producing a visual indication of analyte concentration, said device comprising (i) a first substrate or region, within which is maintained an effective amount of signal generating labeled ligand, (ii) a second substrate or region, within which is disposed an effective amount of immobilized analyte adapted for binding said signal generating labeled ligand, and (iii) a third substrate or region proximate to said second substrate, within which is disposed an effective amount of an activating agent capable of reacting with said signal generating labeled ligand thereby generating light from said diagnostic device; and
- a luminometer disposed sufficiently close to said diagnostic device to accurately detect said light, wherein said luminometer is adapted to measure and quantify said light.

17. The apparatus of claim 16 further comprising:
- a camera assembly disposed proximate to said diagnostic device and adapted to capture an image on photographic film of said light generated from said diagnostic device.

18. The diagnostic device of claim 8 wherein said first substrate comprises solubilized signal generating labeled ligands.

19. The diagnostic device of claim 8 wherein said signal generating labeled ligands in said first substrate are adapted to recognize said analyte.

20. The diagnostic device of claim 8 wherein each of said first substrate, said second substrate, and said third substrate comprises a porous material.

21. The diagnostic device of claim 8 wherein at least one of said substrates can be mobilized to migrate through another one of said substrates such that light is generated by said activating agent of said third substrate in proportion to the concentration of said analyte.

22. The diagnostic device of claim 8 wherein said first substrate, said second substrate, and said third substrate are positioned side by side to each other.

23. The diagnostic device of claim 8 wherein the rate of light production from said diagnostic device, provides a measure of said labeled ligand occupied by said analyte.

24. The diagnostic device of claim 8 wherein said first substrate comprises solubilized signal generating labeled ligands, said immobilized analyte of said second substrate adapted to bind said solubilized signal generating labeled ligands, and said activating agent of said third substrate adapted to react with said solubilized signal generating labeled ligands to emit light.

25. The diagnostic device of claim 8, wherein said first substrate comprises signal generating labeled ligands bound with analyte and unbound signal generating labeled ligands, said second substrate comprises immobilized analyte capable of binding said unbound signal generating labeled ligands, and said third substrate comprises activating agents capable of reacting with said signal generating labeled ligands bound with analyte to thereby emit light.

26. The apparatus of claim 16 wherein said luminometer utilizes at least one of a photomultiplier tube and a photodiode to convert said light to an electrical signal.

27. The apparatus of claim 26 further comprising a display for indicating a numerical value corresponding to said electrical signal.

28. The apparatus of claim 17 wherein the shape of said image is related to said analyte concentration in said liquid test sample.

29. The apparatus of claim 17 wherein the position of said image relative to said film is related to said analyte concentration in said liquid test sample.

30. The apparatus of claim 17 wherein the density of said image is related to said analyte concentration in said liquid test sample.

* * * * *